(12) United States Patent
Brust et al.

(10) Patent No.: US 9,183,262 B2
(45) Date of Patent: Nov. 10, 2015

(54) METHODOLOGY FOR BUILDING AND TAGGING RELEVANT CONTENT

(71) Applicant: Wellclub, LLC, Saint Paul, MN (US)

(72) Inventors: Thomas Edwin Brust, White Bear Lake, MN (US); Phil Kennedy, Eagan, MN (US); Jamal Khan, Redding, CT (US); Jay W. Johnson, Minnetrista, MN (US); Tom Waddell, New Brighton, MN (US)

(73) Assignee: Wellclub, LLC, Saint Paul, MN (US)

( * ) Notice: Subject to any disclaimer, the term of this patent is extended or adjusted under 35 U.S.C. 154(b) by 286 days.

(21) Appl. No.: 13/801,315

(22) Filed: Mar. 13, 2013

(65) Prior Publication Data

US 2014/0156646 A1    Jun. 5, 2014

Related U.S. Application Data

(60) Provisional application No. 61/732,676, filed on Dec. 3, 2012.

(51) Int. Cl.
*G06F 17/30* (2006.01)
*G06F 3/0481* (2013.01)
*G06F 19/00* (2011.01)

(52) U.S. Cl.
CPC ........ *G06F 17/30554* (2013.01); *G06F 3/0481* (2013.01); *G06F 17/30386* (2013.01); *G06F 17/30598* (2013.01); *G06F 19/363* (2013.01)

(58) Field of Classification Search
CPC .................... G06F 17/30598; G06F 17/30386; G06F 17/30554; G06F 17/30076; G06F 17/30082; G06F 17/30581; G06F 17/30672; G06F 17/30734; G06F 17/30867; G06F 17/30893

USPC .................................................. 707/722, 737
See application file for complete search history.

(56) References Cited

U.S. PATENT DOCUMENTS 4,853,854 A    8/1989    Behar et al.
5,251,126 A   10/1993    Kahn et al.
(Continued)

OTHER PUBLICATIONS

"Lift", Powered by Tumblr, [Online]. Retrieved from the Internet: <URL: https://web.archive.org/web/20121116235453/http:/blog.lift.do/, (Nov. 16, 2012), 17 pgs.
(Continued)

*Primary Examiner* — Etienne Leroux
*Assistant Examiner* — Fariborz Khoshnoodi
(74) *Attorney, Agent, or Firm* — Schwegman Lundberg & Woessner, P.A.

(57) ABSTRACT

Systems and methods for content tagging and creation within an information system are described herein. Content tagging may include the processing of unstructured data as input and the transformation of the unstructured data into structured data that has context relative to a user or a group of users. The content may include an action statement suggesting at least one action for the user to perform. The tagging process may associate the action statement with a tag provided from a hierarchy of tag classifications, the tag being relevant to motivating the user to perform at least one action contained in the action statement (for example, the performance actions facilitating the user's achievement of a health goal). The content and associated tagging data may then be stored in the information system for consumption by the content suggestion engine. Further techniques for tagging and accessing tagged data are also described.

23 Claims, 19 Drawing Sheets

(56) References Cited

U.S. PATENT DOCUMENTS

| | | |
|---|---|---|
| 5,596,994 A | 1/1997 | Bro |
| 5,933,136 A | 8/1999 | Brown |
| 6,039,688 A | 3/2000 | Douglas et al. |
| 6,059,724 A | 5/2000 | Campell et al. |
| 6,101,478 A | 8/2000 | Brown |
| 6,144,837 A | 11/2000 | Quy |
| 6,240,394 B1 | 5/2001 | Uecker et al. |
| 6,294,999 B1 | 9/2001 | Yarin et al. |
| 6,381,577 B1 | 4/2002 | Brown |
| 6,547,727 B1 | 4/2003 | Hashiguchi et al. |
| 6,697,783 B1 | 2/2004 | Brinkman et al. |
| 7,216,084 B2 | 5/2007 | Brinkman et al. |
| 7,223,235 B2 | 5/2007 | Brown |
| 7,258,666 B2 | 8/2007 | Brown |
| 7,261,690 B2 | 8/2007 | Teller et al. |
| 7,287,031 B1 | 10/2007 | Karpf et al. |
| 7,297,109 B2 | 11/2007 | Brown |
| 7,299,192 B2 | 11/2007 | Luttrell |
| 7,302,398 B2 | 11/2007 | Ban et al. |
| 7,376,700 B1 | 5/2008 | Clark |
| 7,395,216 B2 | 7/2008 | Rosenfeld et al. |
| 7,412,511 B2 | 8/2008 | Curry |
| 7,478,129 B1 | 1/2009 | Chemtob et al. |
| 7,493,264 B1 | 2/2009 | Kelly et al. |
| 7,555,436 B2 | 6/2009 | Brown |
| 7,584,108 B2 | 9/2009 | Brown |
| 7,590,549 B2 | 9/2009 | Brown |
| 7,636,667 B2 | 12/2009 | Brown |
| 7,647,234 B1 | 1/2010 | Ruderman et al. |
| 7,653,556 B2 | 1/2010 | Rovinelli et al. |
| 7,684,999 B2 | 3/2010 | Brown |
| 7,685,000 B1 | 3/2010 | Petit et al. |
| 7,689,437 B1 | 3/2010 | Teller et al. |
| 7,689,440 B2 | 3/2010 | Brown |
| 7,720,855 B2 | 5/2010 | Brown |
| 7,739,124 B1 | 6/2010 | Walker et al. |
| 7,752,056 B2 | 7/2010 | Brown |
| 7,756,722 B2 | 7/2010 | Levine et al. |
| 7,765,112 B2 | 7/2010 | Brown |
| 7,769,600 B2 | 8/2010 | Iliff |
| 7,778,845 B2 | 8/2010 | Brown |
| 7,788,113 B2 | 8/2010 | Fuhrman et al. |
| 7,801,745 B2 | 9/2010 | Walker et al. |
| 7,809,584 B2 | 10/2010 | Morag et al. |
| 7,822,621 B1 | 10/2010 | Chappel |
| 7,822,625 B2 | 10/2010 | Brown |
| 7,827,039 B2 | 11/2010 | Butcher et al. |
| 7,827,040 B2 | 11/2010 | Brown |
| 7,827,042 B2 | 11/2010 | Jung et al. |
| 7,840,420 B2 | 11/2010 | Brown |
| 7,862,506 B2 | 1/2011 | Brown |
| 7,867,165 B2 | 1/2011 | Brown |
| 7,869,852 B2 | 1/2011 | Brown |
| 7,870,249 B2 | 1/2011 | Brown |
| 7,871,376 B2 | 1/2011 | Brown |
| 7,877,274 B2 | 1/2011 | Brown |
| 7,877,276 B2 | 1/2011 | Brown |
| 7,890,346 B2 | 2/2011 | Padron et al. |
| 7,904,530 B2 | 3/2011 | Partridge et al. |
| 7,921,186 B2 | 4/2011 | Brown |
| 7,925,522 B2 | 4/2011 | Brown |
| 7,941,323 B2 | 5/2011 | Brown |
| 7,941,326 B2 | 5/2011 | Brown |
| 7,941,327 B2 | 5/2011 | Brown |
| 7,944,342 B2 | 5/2011 | Sekura |
| 7,944,448 B2 | 5/2011 | Iwamura et al. |
| 7,945,461 B2 | 5/2011 | Sekura |
| 7,955,219 B2 | 6/2011 | Birrell et al. |
| 7,970,620 B2 | 6/2011 | Brown |
| 7,972,247 B2 | 7/2011 | Daikeler et al. |
| 7,979,284 B2 | 7/2011 | Brown |
| 7,985,164 B2 | 7/2011 | Ashby |
| 7,993,267 B2 | 8/2011 | Iliff |
| 8,013,736 B2 | 9/2011 | Derrick et al. |
| 8,015,025 B2 | 9/2011 | Brown |
| 8,015,030 B2 | 9/2011 | Brown |
| 8,015,033 B2 | 9/2011 | Brown |
| 8,015,138 B2 | 9/2011 | Illiff |
| 8,019,618 B2 | 9/2011 | Brown |
| 8,024,201 B2 | 9/2011 | Brown |
| 8,032,399 B2 | 10/2011 | Brown |
| 8,034,294 B1 | 10/2011 | Goldberg |
| 8,036,912 B2 | 10/2011 | Jensen et al. |
| 8,038,577 B2 | 10/2011 | McIntosh |
| 8,055,516 B2 | 11/2011 | Iliff |
| 8,066,514 B2 | 11/2011 | Clarke |
| 8,069,131 B1 | 11/2011 | Luechtefeld et al. |
| 8,073,707 B2 | 12/2011 | Teller et al. |
| 8,075,451 B2 | 12/2011 | Dugan |
| 8,078,492 B2 | 12/2011 | Brown et al. |
| 8,095,522 B2 | 1/2012 | Welti et al. |
| 8,100,757 B2 | 1/2012 | Melendez |
| 8,108,226 B2 | 1/2012 | Barrett |
| 8,109,874 B2 | 2/2012 | Kong et al. |
| 8,131,570 B2 | 3/2012 | Levin et al. |
| 8,140,663 B2 | 3/2012 | Brown |
| 8,160,901 B2 | 4/2012 | Heywood et al. |
| 8,165,893 B1 | 4/2012 | Goldberg et al. |
| 8,170,807 B2 | 5/2012 | Barnett et al. |
| 8,180,592 B2 | 5/2012 | Yuen et al. |
| 8,182,267 B2 | 5/2012 | Katz et al. |
| 8,182,424 B2 | 5/2012 | Heckerman |
| 8,202,202 B2 | 6/2012 | McGlynn et al. |
| 8,234,127 B2 | 7/2012 | Naik et al. |
| 8,277,377 B2 | 10/2012 | Quy |
| 9,037,578 B2 | 5/2015 | Brust et al. |
| 2001/0027403 A1 | 10/2001 | Peterson et al. |
| 2001/0039503 A1 | 11/2001 | Chan et al. |
| 2002/0026333 A1 | 2/2002 | Endou |
| 2002/0055857 A1 | 5/2002 | Mault |
| 2002/0055859 A1 | 5/2002 | Goodman et al. |
| 2002/0072932 A1 | 6/2002 | Swamy |
| 2002/0087358 A1 | 7/2002 | Gilbert |
| 2002/0128861 A1 | 9/2002 | Lau et al. |
| 2002/0133377 A1 | 9/2002 | Brown |
| 2002/0183598 A1 | 12/2002 | Teraura et al. |
| 2002/0184056 A1 | 12/2002 | Tsuboi et al. |
| 2003/0014279 A1 | 1/2003 | Roman et al. |
| 2003/0061065 A1 | 3/2003 | Keeley |
| 2003/0061215 A1 | 3/2003 | Messina |
| 2003/0065561 A1 | 4/2003 | Brown et al. |
| 2003/0101076 A1 | 5/2003 | Zaleski |
| 2003/0182161 A1 | 9/2003 | Vanderlei et al. |
| 2004/0131997 A1 | 7/2004 | McGuire et al. |
| 2004/0176666 A1 | 9/2004 | Chait |
| 2004/0215491 A1 | 10/2004 | Clark et al. |
| 2004/0242973 A1 | 12/2004 | Tanabe et al. |
| 2004/0243443 A1 | 12/2004 | Asano et al. |
| 2005/0095628 A1 | 5/2005 | Krempin et al. |
| 2005/0113650 A1 | 5/2005 | Pacione et al. |
| 2005/0117527 A1 | 6/2005 | Williams et al. |
| 2005/0240434 A1 | 10/2005 | Wooten et al. |
| 2005/0240438 A1 | 10/2005 | Day |
| 2005/0240444 A1 | 10/2005 | Wooten et al. |
| 2005/0283385 A1 | 12/2005 | Hunkeler et al. |
| 2005/0283386 A1 | 12/2005 | Powers et al. |
| 2006/0004611 A1 | 1/2006 | Brown |
| 2006/0010014 A1 | 1/2006 | Brown |
| 2006/0026036 A1 | 2/2006 | Mahmood |
| 2006/0064322 A1 | 3/2006 | Mascarenhas et al. |
| 2006/0189853 A1 | 8/2006 | Brown |
| 2006/0224416 A1 | 10/2006 | Lloyd et al. |
| 2006/0235722 A1 | 10/2006 | Brown |
| 2007/0005395 A1 | 1/2007 | Singh |
| 2007/0016446 A1 | 1/2007 | Brown |
| 2007/0021984 A1 | 1/2007 | Brown |
| 2007/0055549 A1 | 3/2007 | Moore et al. |
| 2007/0061167 A1 | 3/2007 | Brown |
| 2007/0072156 A1 | 3/2007 | Kaufman et al. |
| 2007/0100595 A1 | 5/2007 | Earles et al. |
| 2007/0190501 A1 | 8/2007 | Brown |
| 2007/0260511 A1 | 11/2007 | Bender, II |
| 2007/0282842 A1 | 12/2007 | Messinaq |
| 2008/0004902 A1 | 1/2008 | Leong-Fern et al. |

(56) References Cited

U.S. PATENT DOCUMENTS

| | | |
|---|---|---|
| 2008/0103814 A1 | 5/2008 | Fabius et al. |
| 2008/0103855 A1 | 5/2008 | Hernandez et al. |
| 2008/0124689 A1 | 5/2008 | Williams et al. |
| 2008/0126276 A1 | 5/2008 | Williams et al. |
| 2008/0126277 A1 | 5/2008 | Williams et al. |
| 2008/0140449 A1 | 6/2008 | Hayes |
| 2008/0162352 A1 | 7/2008 | Gizewski |
| 2008/0168032 A1 | 7/2008 | Criou et al. |
| 2008/0172246 A1 | 7/2008 | Larkin |
| 2008/0183757 A1* | 7/2008 | Dorogusker et al. ...... 707/104.1 |
| 2008/0243543 A1 | 10/2008 | Jung |
| 2008/0287748 A1 | 11/2008 | Sapounas et al. |
| 2008/0318678 A1 | 12/2008 | Stivoric et al. |
| 2009/0005009 A1 | 1/2009 | Marsili |
| 2009/0012988 A1 | 1/2009 | Brown |
| 2009/0030732 A1 | 1/2009 | Jung |
| 2009/0043613 A1 | 2/2009 | Jung et al. |
| 2009/0069643 A1 | 3/2009 | Quy |
| 2009/0070141 A1 | 3/2009 | Jolley |
| 2009/0112617 A1 | 4/2009 | Jung et al. |
| 2009/0118593 A1 | 5/2009 | Jung |
| 2009/0119154 A1 | 5/2009 | Jung |
| 2009/0131089 A1 | 5/2009 | Micali et al. |
| 2009/0132275 A1 | 5/2009 | Jung et al. |
| 2009/0193082 A1 | 7/2009 | Brown |
| 2009/0199230 A1* | 8/2009 | Kumar et al. ................... 725/32 |
| 2009/0312668 A1 | 12/2009 | Ieuthardt et al. |
| 2010/0010829 A1 | 1/2010 | Moore et al. |
| 2010/0063833 A1 | 3/2010 | Mahoney |
| 2010/0150384 A1 | 6/2010 | Waldmann |
| 2010/0235776 A1 | 9/2010 | Brown |
| 2010/0250497 A1* | 9/2010 | Redlich et al. ................ 707/661 |
| 2011/0152635 A1 | 6/2011 | Morris et al. |
| 2011/0172497 A1 | 7/2011 | Ruby et al. |
| 2011/0209037 A1* | 8/2011 | Yoon et al. .................... 715/205 |
| 2011/0276451 A1 | 11/2011 | Busse |
| 2012/0011139 A1* | 1/2012 | Drissi et al. .................. 707/760 |
| 2012/0149972 A1 | 6/2012 | Moore |
| 2012/0221345 A1 | 8/2012 | Mcclure et al. |
| 2012/0272278 A1* | 10/2012 | Bedi ............................. 725/105 |
| 2013/0124218 A1 | 5/2013 | Masloski et al. |
| 2014/0100955 A1* | 4/2014 | Osotio et al. ............... 705/14.55 |
| 2014/0156308 A1 | 6/2014 | Ohnemus et al. |
| 2014/0156645 A1 | 6/2014 | Brust et al. |
| 2014/0156676 A1 | 6/2014 | Brust et al. |
| 2014/0157171 A1 | 6/2014 | Brust et al. |

OTHER PUBLICATIONS

"U.S. Appl. No. 13/772,405, Final Office Action mailed Jul. 9, 2015", 23 pgs.

"U.S. Appl. No. 13/772,405, Response filed Aug. 10, 2015 to Final Office Action mailed Jul. 9, 2015", 16 pgs.

"U.S. Appl. No. 13/772,405, Examiner Interview Summary mailed Apr. 21, 2015", 3 pgs.

"U.S. Appl. No. 13/772,405, Non Final Office Action mailed Jan. 7, 2015", 22 pgs.

"U.S. Appl. No. 13/772,405, Response filed May 7, 2015 to Non Final Office Action mailed Jan. 7, 2015", 22 pgs.

"U.S. Appl. No. 13/772,697, Examiner Interview Summary mailed Dec. 17, 2014", 3 pgs.

"U.S. Appl. No. 13/772,697, Non Final Office Action mailed Sep. 3, 2014", 12 pgs.

"U.S. Appl. No. 13/772,697, Notice of Allowance mailed Jan. 20, 2015", 7 pgs.

"U.S. Appl. No. 13/772,697, Response filed Dec. 23, 2014 to Non Final Office Action mailed Sep. 3, 2014", 16 pgs.

"U.S. Appl. No. 13/801,048, Examiner Interview Summary mailed Mar. 27, 2015", 3 pgs.

"U.S. Appl. No. 13/801,048, Non Final Office Action mailed Nov. 25, 2014", 8 pgs.

"U.S. Appl. No. 13/801,048, Notice of Allowance mailed Jun. 5, 2015", 7 pgs.

"U.S. Appl. No. 13/801,048, Response filed Mar. 25, 2015 to Non Final Office Action mailed Nov. 25, 2014", 15 pgs.

* cited by examiner

| ACTION STATEMENT | DIFFICULTY | DURATION | BEHAVIOR CHANGE | RESTRICTIONS |
|---|---|---|---|---|
| WALK IN THE PARK | LOW | 15 MIN | GROUP | MOBILITY |
| EAT OATMEAL BREAKFAST | LOW | 10 MIN | | DIET |
| 40 MINUTE ROLLERBLADE | MEDIUM | 40 MIN | GROUP | HIGH MOBILITY |
| EAT WHOLE GRAIN CEREAL | LOW | 10 MIN | | DIET |

FIG. 5

500 — Suggestions

| Suggestion # | Suggestions (502) | Title (504) | Lifestyle Category (Eating, Movement, Self View) | Sub Problem Category | Sub-Sub Problem Category | Likes/Dislikes | Attribute 1 | Attribute 2 | Attribute 3 | Attribute 4 | Attribute 5 | Attribute 6 | Difficulty | Time Duration | Actual Time | Timeliness | Restriction? |
|---|---|---|---|---|---|---|---|---|---|---|---|---|---|---|---|---|---|
| E1 | Tonight for dinner make sure the majority of your plate is made up of green vegetables. | Green vegetables for dinner tonite. | E | ELI | ELI1, ELI4 | y | y | n | n | n | y | n | Beginner | <15 Mins | | EVE | x |
| E2 | Eat from a small salad plate instead of a dinner plate. This forces you to take smaller portions. | Try using a salad plate to keep your portion size down. | E | EPC | EPC1 | y | y | y | n | n | y | y | Beginner | <15 Mins | | MOR, NOO, EVE | x |
| E3 | Use a vinaigrette on your salad instead of a creamy dressing. | Reduce your calories with a vinaigrette dressing | E | ELI | ELI1, ELI2, ELI4 | y | y | n | n | n | y | n | Beginner | <15 Mins | 15 | NOO, EVE | x |
| E4 | Make a yogurt parfait for breakfast. | Yum - yogurt parfait | E | ETR | ETR2, ETR3 | y | y | y | n | n | n | n | Beginner | <15 Mins | 15 | MOR | x |
| E5 | Stay hydrated in between meals today. This will keep you full longer. | Drink liquids between meals today | E | EI | EI3 | n | y | y | n | n | y | y | Beginner | <15 Mins | 15 | MOR, NOO, EAF, EVE, RBB | |

Tags

1400

Create Suggestion

Category*  | Movement ▽ |
15 other suggestions found

Title*  | Bowling for Weight Loss |  3 similar suggestions found

Description | When out bowling, choose as heavy of a bowling ball as possible |

Timeliness | 24 Hours ▽ |

Duration* | < 60 Minutes ▽ |

Image URL | Image URL |  Browse

Video URL | Video URL |

Descriptor | Bowling |

Difficulty | Intermediate ▽ |

SUBMIT

Search

| running |
| Tom Smith |
| Movement ▽ |
| Approved ▽ |

[ FIND SUGGESTIONS ]

Search Results    5 Results Found

| Title | Author | User Type | Duration | Attempted | Completed | Failed | |
|---|---|---|---|---|---|---|---|
| Push yourself while running | Tom S. | Admin, Basic Supporter | 15 | 1 | 0 | 0 | Actions ▽ |
| Change your running route | Tom S. | Admin, Basic Supporter | 15 | 1 | 1 | 0 | Actions ▽ |
| Change your running style | Tom S. | Admin, Basic Supporter | 15 | 1 | 0 | 1 | Actions ▽ |
| Add a quick walk into your routine | Tom S. | Admin, Basic Supporter | 15 | 0 | 0 | 0 | Actions ▽ |
| Try sprints on a track | Tom S. | Admin, Basic Supporter | 15 | 0 | 0 | 0 | Actions ▽ |

*FIG. 15*

METHODOLOGY FOR BUILDING AND TAGGING RELEVANT CONTENT

CROSS-REFERENCE TO RELATED APPLICATIONS

This application claims the benefit of U.S. Provisional Patent Application Ser. No. 61/732,676, filed Dec. 3, 2012, which is incorporated by reference herein in its entirety. This application is related to pending U.S. patent application Ser. No. 13/772,697, titled "CONTENT SUGGESTION ENGINE," and filed Feb. 21, 2013; and Ser. No. 13/772,405, titled "GOAL-BASED CONTENT SELECTION AND DELIVERY," and filed Feb. 21, 2013; the disclosures of which are incorporated by reference herein in their entireties.

TECHNICAL FIELD

Embodiments pertain to techniques and systems for content selection and management. Some embodiments relate to data-driven operations in an information system to identify, label, and tag relevant content provided for output to human subjects.

BACKGROUND

Various data services select or recommend content for display to users. For example, in the self-help setting, a variety of existing data services provide tips, recommendations, and focused content to assist a subject human user with goal-based outcomes such as weight loss, smoking cessation, medical therapy, exercise goals, and the like. Some of these data services provide recommended content to a user in response to user-indicated preferences, user-indicated activity history, or manual user requests for content. Other data services rely on an expert human user to determine which content is most appropriate for delivery to the subject human user to achieve a certain outcome.

To the extent that existing data services provide automated recommendations or selections of content, the timing, delivery, and substance of the content is determined by complex predetermined rules and attributes, or other selections influenced by manual human intervention. For example, recommendations may be hard-coded in a content delivery system to deliver suggestive content in a particular fashion responsive to some detected condition. A human user must manually designate and select content from such content delivery systems for display at appropriate times. Existing systems and techniques do not provide adequate structures, categorizations, or rules for retrieving or displaying stored content without extensive programming or oversight.

BRIEF DESCRIPTION OF THE DRAWINGS

FIG. 5 illustrates associations between example content and tags according to an example described herein.

FIG. 14 illustrates a user interface for a tagging facility to perform tagging of various content items according to an example described herein.

FIG. 15 illustrates a user interface for form-based editing of content properties and tags according to an example described herein.

DETAILED DESCRIPTION

Figure 1:
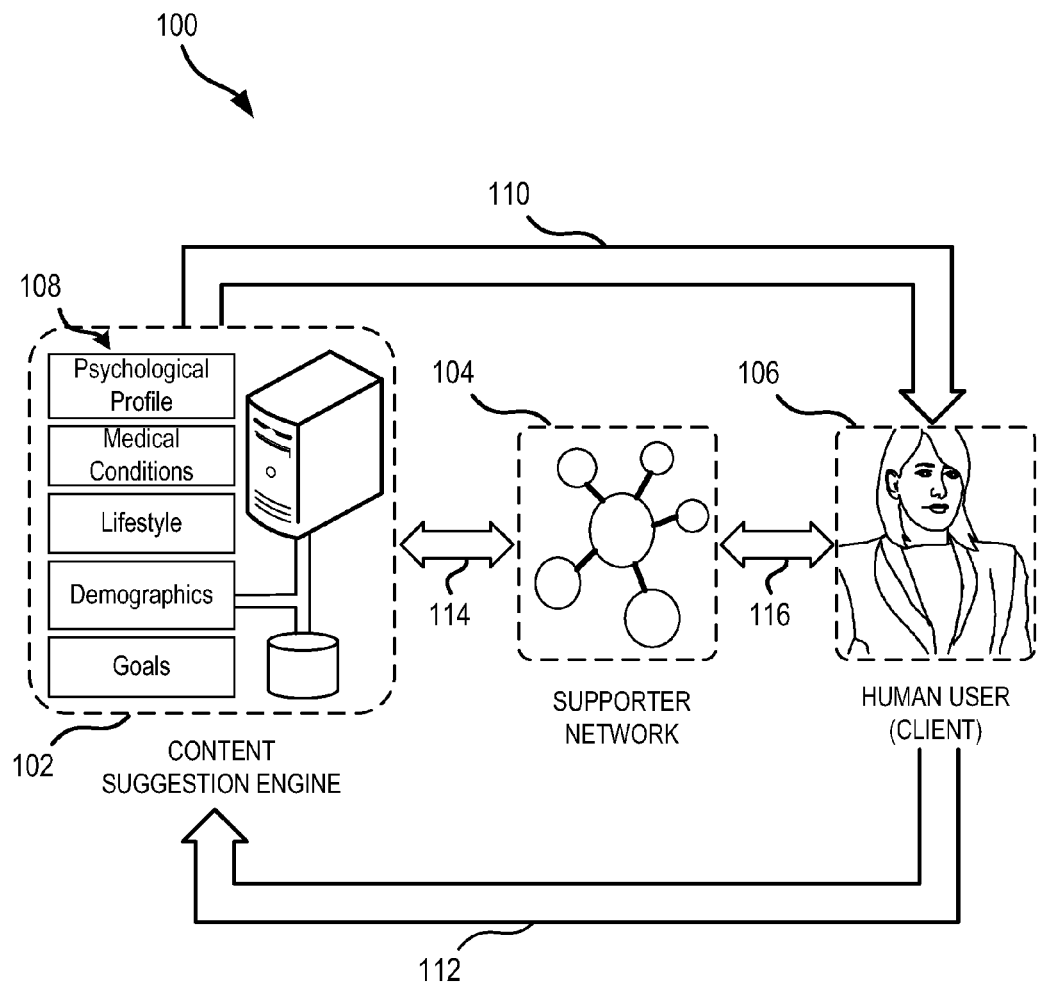
FIG. 1 illustrates an information flow diagram of interaction with an example information system and a content suggestion engine according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The present disclosure illustrates techniques and configurations to enable the filtering of content and related content delivery actions, to generate content relevant for human activities to accomplish some predetermined or ongoing goal or set of goals. The type, substance, and delivery of the content serve to provide a human user with motivating suggestions, encouragement, and positive reinforcement towards attaining this goal or set of goals.

The computing systems and platforms encompassed by the present disclosure include a mobile or web-based social networking information service, interacting with a suggestion engine, that is used to motivate a human user to change behavior (such as adopting healthy lifestyle choices and activities that are likely to lead to a positive health outcome) through a persistent intelligent coaching model. The information service can provide intelligent decision-making and reinforcement of certain content and content actions, to facilitate encouragement or motivation that increases the likelihood of change in human behavior to achieve the goal. In particular, the information service focuses on encouraging a human user to complete a series of discrete, separate actions that achieve small goals, which, in combination, may help achieve a larger overall goal. For example, in a weight loss setting, this can include a series of tens, hundreds, or thousands of discrete diet and exercise actions that, in combination, may help the human user achieve a weight loss goal.

In conjunction with operations of the suggestion engine, the information service can adapt to learn a user's behavior patterns and offer personalized, relevant, or timely suggestions, motivations, or other directed content to help the human user achieve the goal. The information service also can enable peer and professional support for a human user by creating and maintaining human connections relevant to the goal, such as through establishing social networking connections and social networking interactions customized to the goal. As the social network or the behaviors of the human user change, the information service can adapt to alter the actions, motivations, or other directed content to remain relevant, personal, or timely to the human user. In this fashion, the information service is intended to cause behavior changes of the human users through promotion of actions to achieve the user's goals, with social encouragement by friends, family, or team members (supporters), personal motivations reinforced with reminders, or new structures in their living environment, such as can be helpful in altering habits to achieve the goal.

The information service can include various applications and corresponding user interfaces to be viewed by the human user and supporters of the human user to encourage beneficial interactions between the human user and the supporters. These interactions, which may be driven by suggested content and suggested content delivery types or timings, are used to cause activities that lead to the intended behavior change(s) in a human user. Accordingly, the content suggestion engine acts in a larger system of an "intelligent" information system that provides appropriate messages and content selections to the human user and supporters at the right time.

FIG. 1 illustrates an information flow diagram of interaction with an example information system 100 configured for providing content (e.g., motivations, recommendations, suggestions, facts, or other relevant material) to human users. The information system 100 can include a suggestion engine 102, participation from a supporter network 104 of various human or automated users, and participation from a subject human user (further referred to herein as a "client") 106.

The suggestion engine 102 can be configured to make decisions to deliver relevant content dynamically (e.g., at the proper time, in the proper context, and with the proper communication medium) using data conditions 108 maintained for the client 106. The data conditions 108 maintained for the client 106 may include information such as: one or more goals of the client; demographic information such as gender, age, and familial information; medical information such as medical conditions, medical history, and medical or physical restrictions; a psychological profile and other psychological information such as personality type, daily routines or habits, emotional status, likes and dislikes; and available external devices (e.g., smart phone or smart phone applications, smart weight scales, smart TV, video game systems, etc.); client desired coaching programs and models (e.g., diet style, exercise focus, or mental health); and information relevant to discrete activities, such as present or scheduled locations of the client, and time to accomplish activities; and information relevant to the goal, such as time to achieve the goal, difficulty of achieving the goal; and like information for conditions relevant to the human user, supporters of the human user, or the overall goal.

The specific content selection operations of the suggestion engine 102 are directed to change the behavior of the client 106, such as to help the client 106 achieve a defined or derived goal with a series of content messages that are intended to invoke action by suggested activities and events. Delivery of the content may be provided directly from the suggestion engine 102 to the client 106 with a content delivery flow 110. With the content delivery flow 110, the suggestion engine 102 can query the client 106 periodically or randomly to gain information and feedback that can affect what content is delivered to the client 106. Responses by the client 106 may be provided back to the content suggestion engine through a content feedback flow 112 to indicate the results of such querying or feedback.

The suggestion engine 102 may also provide indirect content delivery flows 114, 116 through a supporter network 104, to enable the supporter network 104 to provide content to the client 106 at appropriate times. Specifically, the suggestion engine 102 can indirectly provide content selections to the user using an indirect content flow 114, and orchestrate resources of the supporter network 104 by engaging influential persons (e.g., family, friends, or others that influence the human user (the client 106)) to forward or deliver the content to the client 106.

The supporter network 104 may also facilitate interaction between the client 106 and healthcare providers or other professionals (e.g., nutritionists, personal trainers, psychologists, or behavior coaches, among others). Such interaction from the supporter network 104 may be used to proactively guide personalized and critically timed suggestions (e.g., such as by sending a message that encourages a specific activity to the client 106), or persistently coaching, guiding, motivating, or focusing the client 106 to complete actions to achieve his or her goal.

Additionally, members of the supporter network 104 may generate and provide suggestions back to the content suggestion engine 102, directly or with crowdsourcing-type mechanisms distributed among a plurality of persons. For example, a supporter can directly author suggestions that are sent to the client 106, or edit, modify, or unify suggestions with slight modifications for use with the human user. Based on the effectiveness of the content created by the supporter network 104, a pool of suggestions may be created.

Thus, the supporter network 104 may be used to generate or forward content selected by the content suggestion engine 102, using indirect content flow 116. For example, the suggestion engine 102 may provide a supporter member of the supporter network 104 with pre-formatted action content that can be sent directly from the supporter to the client 106 using a recognized communication medium, such as by forwarding and customizing a text message, an email message, a social network message, and the like. Suggestions directly received from members of the supporter network 104 are more likely to reduce barriers or excuses of inaction, and empower the client 106 to perform an action or actions that will help achieve their goals. Feedback may also be provided back to members of the supporter network 104 from the client 106 (such as a confirmation that the client 106 performed the activity, a message that the client 106 enjoyed the suggestion, a message asking for support to perform the activity, and the like).

The suggestion engine 102 can communicate with the supporter network 104 and the client 106, such as to obtain information about the client 106 or provide messages to the client 106 or to the supporter network 104. The supporter network 104 can personalize the message and send the message to the client 106, such as shown in FIG. 1. By having the client 106 receive the message from the supporter network 104, the message can have more impact and potentially be more motivating than if it came directly from the suggestion engine 102.

Suggestion Content Types and Delivery

Appropriate messages, multimedia, and other content delivered to the client 106 from or on behalf of the information system 100 are referred to herein as "suggestion content," as the content can be selected and produced by the content suggestion engine 102. Suggestion content can include content from one or more messages that the client 106 and supporter network 104 receive that are collectively intended to attract human attention and cause the client 106 to perform some action. The suggestion content can be tailored and customized to be appropriate to the client 106, time, and individual intended actions. The suggestion content can include a variety of formats, such as content that indicates greetings, actions, motivations, prompts, reminders, and rewards.

Described herein are types of suggestion content, how suggestion content can be aggregated, and techniques for creating and delivering the suggestion content. Further described herein are system, apparatus, and device configurations to implement the suggestion engine that can enable a particular selection of suggestion content to be sent to the supporter network 104 or client 106. As used herein, suggestion content can include content delivered to the client 106 intended to cause an action related to an ultimate goal. Suggested action content sent to the client 106, as further described herein, may be constructed from content that includes an action statement 406, and a pre-statement 404 or a post-statement 408 (as further described below with reference to FIG. 4A).

As used herein, motivational content is a specific subset of suggestion content that is intended to improve the likelihood of the client 106 performing a suggested action by appealing to some human interest. Motivational content may be embodied by: various prompts that include a request for a response from the client 106 or supporter network 104; reminders that include a statement that reminds the client 106 or a supporter from the supporter network 104 that an action on their part is due; rewards that include statements provided to the client 106 or supporter that are congratulatory or explain something being given to the client 106 or supporter; or supporter messages that include content specifically intended for the supporter.

Content provided by the information system 100 may be stored and maintained in structured or unstructured form. Unstructured content can include suggestion content not yet edited, tagged, or final reviewed; whereas structured content can include content that has been edited, tagged, and reviewed, and ready for use by the suggestion engine 102 (as further illustrated with reference below to FIG. 2).

Content can be tagged for use in defined retrieval operations. Such tagging can include a psychological assessment matching. A client 106 can be asked to take assessments for engagement, receptivity, or social style. The content can be tagged in such a way that the information system 100 matches the client 106 with the style of the content suited for them, thereby "personalizing" the interactions between the information system 100 and the client 106, such as to provide a more effective or engaging environment. The information system 100 can provide content for each of eating, movement (e.g., actions for the client 106 to physically accomplish), and self-view. The tags can provide and store this information.

As further discussed herein, the tagging can include "behavior change" tagging. A current behavior change theory promotes a combination of "sources of behavior change" that promote a higher probability of changing people's behavior. These sources of behavior change include items that improve an individual's intrinsic/extrinsic motivation and aptitude, group factors and power to cause behavior change, and environmental factors and power to cause behavior change. Presenting suggestions that fit in multiple behavior change areas can be more effective than presenting suggestions in just one or a few of the areas. Additionally, the client 106 can complete a lifestyle questionnaire, which determines, such as by using Boolean logic, different "problems" that the client 106 may have. Content can be tagged with these problems, such as to tag content that relates to the problem. The client 106 can work on the problem by choosing specific suggestions or playlists of suggestions tagged with that problem.

In one example use of a suggestion engine 102, the client 106 is the person that the information system 100 is intended to help; the supporter network 104 can include one of the persons providing aid to the client 106—this person could be a team member, friend, family member, or paid supporter such as personal trainer, among others. Thus, overall users of the suggestion engine 102 can include any person using the information service (and accompanying applications, websites, and services), including the client 106, supporters in the supporter network 104, an administrator, and the like.

The information system 100 facilitates interaction among the client 106 and supporters in the supporter network 104, such as encouraging clients and supporters to interact in the social network, to accompany several types of content. Content can be created that gives clients and supporters specific actions to perform, and this content can be delivered in a way that encourages the supporter or client 106 to perform the action. The content can be designed to be delivered to the client 106 either directly or through the supporter. A plurality of action statements (further described with reference to a formatted suggested action message 402 depicted in FIG. 4A) providing respective suggested actions can be presented to the client 106 for participation. Other types of content can be used to increase the probability of the client 106 performing the suggested actions.

Figure 2:
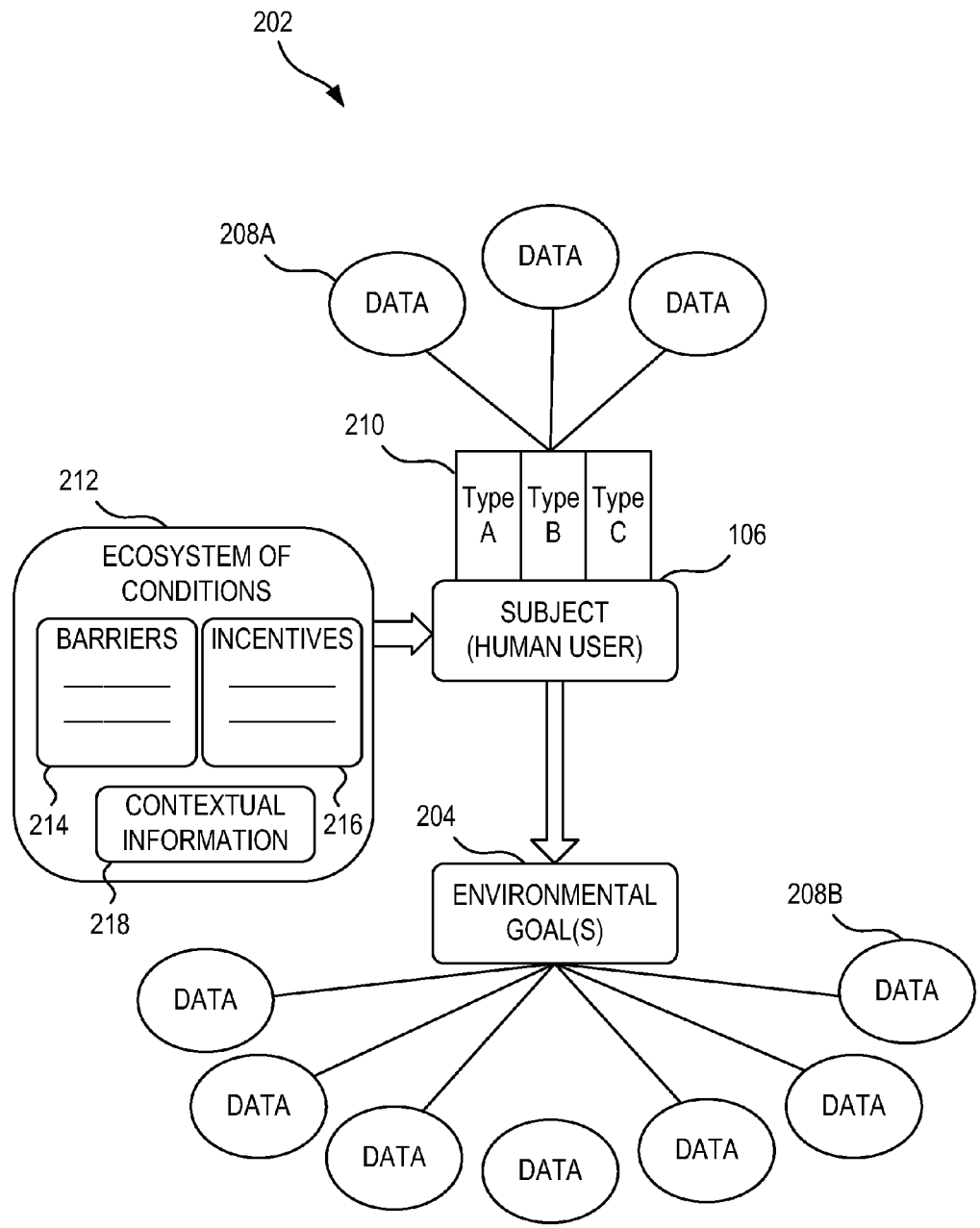
FIG. 2 illustrates an information flow diagram including data operations within a content suggestion engine of an information system according to an example described herein.

FIG. 2 illustrates an information flow diagram of an example of data operations 202 of the suggestion engine 102. Data 208A and 208B, illustrated as various inputs, can be provided in a structured format. Structured data in one example is unstructured data that has undergone a process of formalization, structuring, categorization, and tagging in the information system 100. The data operations 202 serve to map data 208A to a personality type 210 or characteristic of the client 106, and an ecosystem of conditions 212 is factored to produce appropriate data 208B that addresses one or more environmental goals 204.

Data input for operations 202 of the suggestion engine 102 may originate from a variety of data sets and data types, but some data types and data inputs may not motivate a human subject to attain a particular goal at a particular time. Data 208A can be provided from client personal data, such as location, psychological state, lifestyle, occupation, relationship status, or coaching style, among others, collected or determined for the client 106. A client's personality type 210, such as caregiver, colleague, competitor, authoritarian, optimist, skeptic, fatalist, activist, driver, analytical, amiable, expressive, or combinations thereof, can be inferred or otherwise determined from the data 208A (and changed or adapted as necessary using contextual information 218 or data 208B).

An ecosystem of conditions 212, including barriers 214 to and incentives 216 for achieving the one or more environmental goals 204 can be determined. The ecosystem of conditions 212 generally reflects information items that the information system 100 is aware of, and relevant factors to achieve success. This may include data such as the time of day, client location, medical records of the client 106, and like information or conditions that may affect the client 106.

Barriers 214 considered with the ecosystem of conditions 212 can include the client 106 having a physical ailment, such as a bad knee or asthma, not having a phone, not having supporters, does not like working out, cannot afford the services, having a busy schedule, medical conditions (such as allergies or taking medications), among others. Incentives 216 considered within the ecosystem of conditions 212 can include things that the client 106 likes (e.g., brand name shoes or specific music), peer pressure, a good feeling gained from performing some activity (e.g., working out), a discount on goods or services provided, or an upcoming event (e.g., a half marathon). The data 208A, 208B and the ecosystem of conditions 212 can be determined through obtaining answers to questions, such as through answers to episodic questions posed to the client 106 (the episodic questions occurring at determined times, places, or contexts). The ecosystem of conditions 212 may further provide contextual information 218 to provide additional data to help interpret or understand the barriers 214, incentives 216, or the data 208A, 208B.

The data 208B can be directly or indirectly related to the one or more environmental goals 204. The data 208B can include a reward for achieving the goal(s) 204 (e.g., kudos), a type of diet to be followed, a reason for wanting to achieve the goal, or a date by which to achieve the goal, among others. The environmental goal(s) 204 may include physical activity goals, such as to lose a certain amount of weight, change a habit, such as to quit smoking, quit biting fingernails, workout a specific number of times during a period of time, or to achieve a physical challenge such as running a marathon or climbing a mountain, among others.

The one or more environmental goals 204 are not necessarily limited to a central, ultimate goal (such as losing weight, or stopping smoking), but can include a number of subordinate or associated goals (such as developing healthy habits, a positive self-image, or confidence or enjoyment of the goal-reaching process) that help the client 106 achieve the ultimate goal in a positive fashion. Thus, the environmental goals 204 may be broader than a single goal and can include a number of additive, complimentary, or interrelated actions and results that produce beneficial outcomes and experiences for the human user.

Humans have preferred modes of conversation and interaction. A personality style to invoke these preferred modes can be inferred or determined from answers to questions in questionnaires. The information system 100 can assist the client 106 in completing several questionnaires that show these preferences. The personality styles can indicate a client's receptivity (e.g., the preference for a certain tone of message); engagement (e.g., a bias towards immediate action versus thoughtful consideration when presented with a challenge to change); or social style (e.g., an intersection of assertiveness and responsiveness). The suggested action content delivered from the information system 100 and the content suggestion engine 102 can be designed to fulfill all these preferences.

Structured and Unstructured Data

Figure 3:
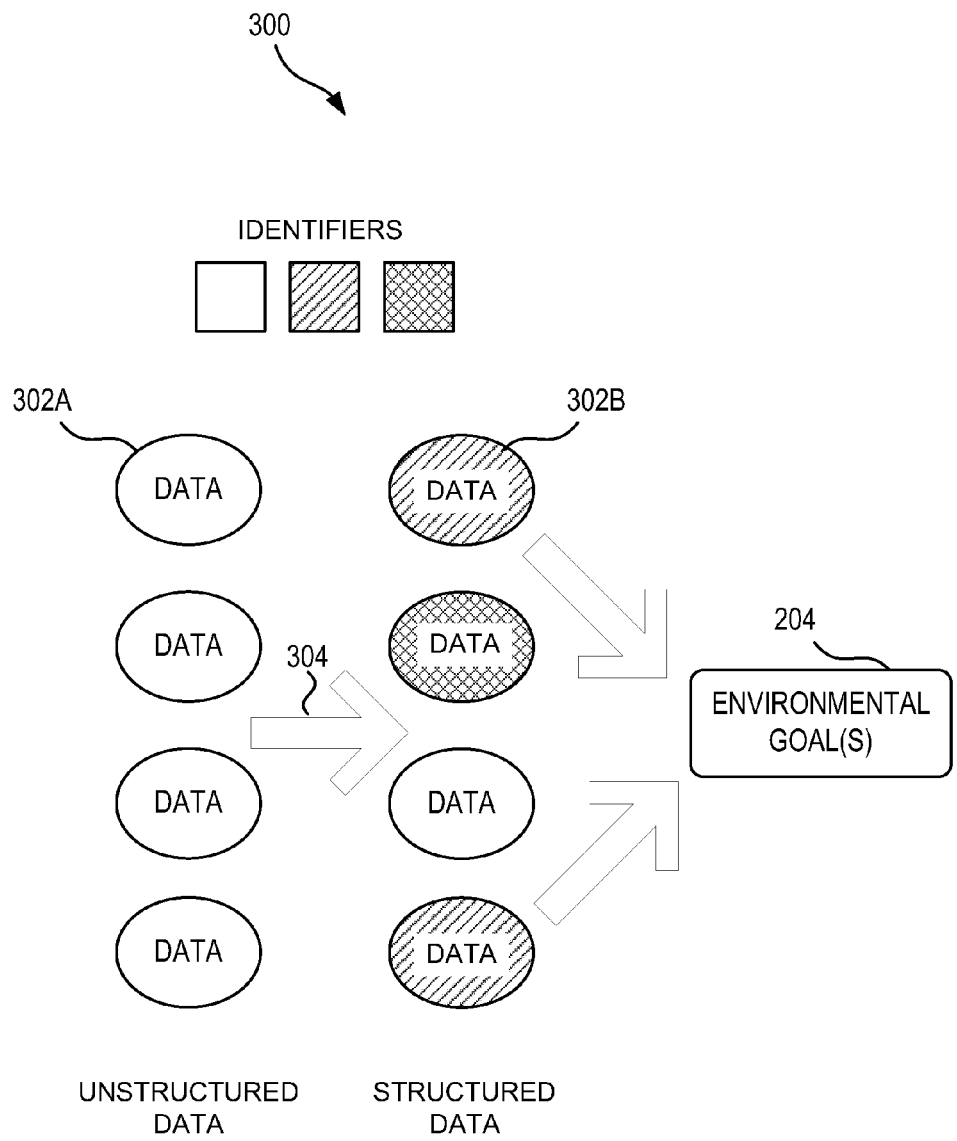
FIG. 3 illustrates a process of tagging unstructured data to produce structured data that is consumable by a content suggestion engine according to an example described herein.

FIG. 3 illustrates a process 300 of tagging unstructured data 302A to produce structured data that is consumable in an information system by a content suggestion engine 102 according to an example described herein. As illustrated, a tagging process 304 serves to transform unstructured data 302A into structured data 302B, with the structured data 302B relating (in varying degrees) to an environmental goal 204.

Unstructured data 302A includes suggestion content not yet edited, tagged with the tagging process 304, and final reviewed. Structured data 302B includes content that has completed editing, tagging, and review, and is ready for use by the suggestion engine 102. The unstructured data 302A becomes structured and has context relative to the client 106 through a process of formalization, structure, categorization and tagging 304 of this disparate data.

An Environmental Goal 204 is a targeted result established by a client 106 within a specified variable timeframe (e.g. lose two pounds in one week; arrive at recon point within 24 hours, etc.). The Environmental Goal 204 may have structured data 302B associated with it (e.g. time zone, season, color, coordinates, weight in pounds, current weather, psychological state, etc.) The environmental goal 204 may be behavior related (e.g., habitual patterns over time).

Figures 4A, 4B:
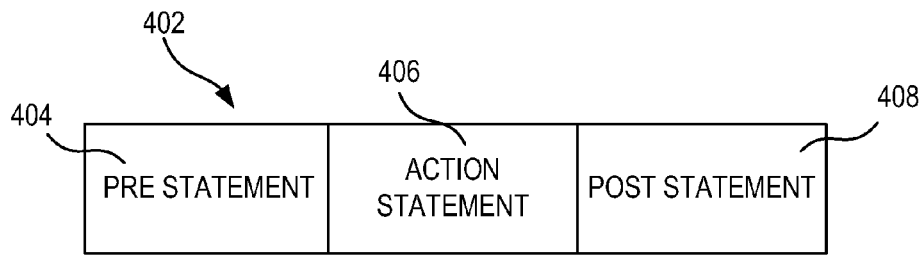
FIG. 4A illustrates a data format diagram including a format for action statement data consumed by a content suggestion engine according to an example described herein.
FIG. 4B illustrates a data format diagram including a format for tagging of data consumed by a content suggestion engine according to an example described herein.

FIG. 4A illustrates a data format diagram including an example of a format for a suggested action message 402 that can be sent to the supporter network 104 or the client 106. A suggested action type of content can be provided from the suggestion action message 402, which is sent to the client 106. The suggestion action message 402 may include an action statement 406, and a pre-statement 404 or a post-statement 408 (as further detailed below with reference to FIG. 4B). An action statement 406 can provide the part of the suggested action message 402 that provides the "do this" statement; a pre-statement 404 and post-statement 408 can provide the part of the suggested action message 402 that personalizes the tone of the "do this" statement (these statements precede and follow the action statement, respectively). Examples of action statements 406 are shown in FIG. 4B.

The pre-statement 404 or post-statement 408 can be tailored to fit the personality type 210 of the client 106. For example, if the client 106 is determined to have a competitor personality type 210, the pre-statement 404 can be "Your teammates and supporters are watching"; "We need you"; or "It's coach [insert name] here . . . "; among others.

The action statement 406 can convey the suggested action to the client 106, such as: "you are going to the park today"; "you are going for a run today"; "you are going to eat a salad today"; among others. The post-statement 408 can be an encouraging or motivating statement that is tailored to the personality type 210 of the client 106.

In the example of the client 106 with the competitor personality type 210, the post-statement can be statements such as: "You cannot win if you do not try"; "You will have the best day of anyone this week"; or "On your marks, get set, go"; among others.

Further, the structure of content can include an action statement (e.g., a recipe), pre-statement, or post-statement, customized to: specific psychological typing; motivational content; prompts; greetings; rewards; or messages to supporters. A suggested action message 402 can be "personalized" to a client's personality type 210. An action statement 406 can be preceded with a pre-statement 404 (e.g., a greeting), and followed with a post-statement 408 (e.g., appropriate reminders, prompts, or motivations). Completion of, or non-completion of a suggested action message 402 can be followed by either a reward (e.g., kudos) or motivation intended to keep the client 106 trying again, respectively.

Content Delivery Programs for Suggested Content

A playlist is a set of suggested actions (each action containing suggested content) that can be presented to the client 106 as a single "set of suggested actions." This can make the choosing of actions less frequent, and provide a short-term context for the client 106. The client 106 may desire repetition, variety, to concentrate on a particular area, or to be generally healthy. Playlists can be designed to link suggested actions together to create a coordinated effort that can incorporate client desires.

The playlist(s) can be chosen as a specific item by the client 106. The playlist may include suggested actions during a period of time, such as a day, week, ten days, months, quarter, year, etc. The client 106 may wish to choose a fully or partially coordinated effort that is longer than a single action, e.g., making sure they eat a healthy breakfast for one week. The playlist feature can allow the client 106 to choose this as a single item. Each suggested action message 402 in the playlist can be set for specific times as designated in the playlist (e.g., every x period).

A program can be: 1) a designation of a specific type of suggested action message 402 defined in keywords (e.g., Mayo Clinic diet, Weight Watchers® diet, etc.), where the suggestion engine 102 preferentially chooses actions or playlists to present to the client 106 as a function of the keywords; or 2) a set of playlists presented in a series, such as a series that has a defined objective (for example, eat a good breakfast for four (4) weeks, which can include suggested action messages for both purchasing the materials for a good breakfast, such as oatmeal, as well as allowing enough time to eat it before starting the day's other activities).

For programs of type 1, the client 106 can be offered the option of choosing a program to follow. For programs of type 2, users, such as employees or professional supporters, can create programs by selecting a series of playlists, and then providing a definition, keywords, or additional tags to be included by the program. The program can include a "creator" designation for the user who created the program and the "creator" can title the program. Choosing a program can give the client 106 context for why he or she is performing the specific eating/movement/self-view action(s).

A goal 204 set by the client 106 can be a powerful motivation. The goal 204 can be used to determine what percentage of the suggested action messages will be selected from each of the eating/movement/self-view areas, for example. The goal 204 can be used to motivate the client 106 by reminding the client 106 of the specific goal 204 he or she has chosen.

The suggestion engine 102 can deliver appropriate suggested action content to the supporter network 104 or client 106 as a function of a set of rules. These rules can include how the content will be delivered to the client 106 or supporter network 104. The suggestion engine 102 can determine one or more suggested action message or playlists based on the client's psychological, lifestyle, or preference and restriction assessment, or the client goal(s) 204. The suggested action message 402 can be sent to the supporter for forwarding on to the client 106 or directly to the client 106 depending on rules or preferences.

The content can follow a general flow. The client 106 can be presented with a number of suggested action messages 402 (or playlists), from which the client 106 can choose one or more. The suggested action messages 402 can be presented as just the action statement 406, with no personalization. A timer of a specified period, such as twenty-four hours, can start at or near the time the suggested action is chosen. The suggested action can have a designated time of day associated with it, such as morning if the action is breakfast, for when a reminder should be sent—the client 106 can designate times that he or she regularly does things like eat breakfast, lunch, or dinner, when they exercise, and when he or she struggles with being hungry. If the client 106 did not set preferred times when choosing a suggested action message 402, the system can ask the client 106 when that type of action is typically done.

One or more reminders can be sent to the client 106. The reminder can include personalization—the reminder can be provided at the beginning of the next day, or at or near a designated time. A motivation or prompt can be sent to the client 106 at times before or after a reminder. A prompt can be sent to the client 106 after a specified period of time has lapsed. This prompt can ask the client 106 if he or she has completed the suggested action. If the client 106 has completed the suggested action, the client 106 can be rewarded with reward points (also referred to herein as "kudos") or given a congratulatory motivation. If the client 106 has not completed the suggested action, the client 106 can be given a conciliatory motivation, such as "you will get it next time!" The client 106 can be asked if: 1) they would like to try again; or 2) move on to the next suggested action, or something similar. If the client 106 responded that he or she would like to try again, the previous action can be presented at an appropriate time with appropriate motivations and prompts. If the client 106 responded that he or she would like to move on to the next suggested action, the information system 100 can log the incomplete suggested action as not completed and send the next task to the client 106. If the client 106 has chosen a playlist of suggested action messages 402, the steps above can be substantially followed, without being asked if he or she would like to try again. If the client 106 does not perform a suggested action, he or she can be presented with a conciliatory motivation, and then reminded of the next task in the play list. When the client 106 is sent a suggested action message 402 from a playlist, the playlist name, or the order of the suggested action message 402 can be included in the information available to the client 106.

An action statement 406 defines the action being sent to the client 106, such as "Take a walk in a park"; "Try this recipe"; or "Write the day's best moments in your journal before you go to bed"; among others. A pre-statement 404 and a post-statement 408 can provide a short statement that personalizes the suggested action message 402 for a specific personality type 210. The personalization can be accomplished by having a person use a database of personalization examples to create the entire suggested action message 402, and filtering the created suggested action messages 402, such as by using the content suggestion engine 102, to help ensure the language used is appropriate. Selecting tagged content of a particular suggested action can be accomplished by selecting content based on the unique tag for the action statement 406, selecting content based on the a tag that defines the relevant personality type 210 of the client 106, or both.

After the client 106 has chosen a suggested action, the information system 100 can provide an appropriate motivation, prompt, reminder, or reward statement. The number of motivations, reminders, and prompts can be defined in a suggestion engine 102 database, and can be based on psychological assessments of the client 106. A psychological assessment can include determining a receptivity of the client 106 to a motivational or encouraging statement, such as whether the client 106 is a caregiver, colleague, competitor, or authoritarian; a client's engagement in achieving their goal 204, such as whether the client 106 is an optimist, fatalist, activist, or skeptic; a client's social style, such as whether the client 106 is a driver, amiable, analytical, or expressive; or a combination thereof. For example, a message for a caregiver can take the form of admonition, communicate to the client 106 that the substance of the message is good for him or her, or be supportive yet directive. Such persons can tend to assume a hierarchical relationship in which they have some form or power over another, yet tend to be more challenging than nurturing in their interactions. A message for an optimist can include encouragement to act, support or pressure from their social network, increasingly persistent reminders to act, or a combination thereof. Such persons may tend to think about the suggested action, search for ways to ensure success, over-think or over-plan, or have a high level of excitement that can diminish without action. A message for an analytical person can include statistics or data that provide support for why the action should be accomplished, or it can be more task-oriented rather than person-oriented. Such persons can be perfectionists, critical of themselves, systematic, well organized, prudent, or a combination thereof.

Data Formats and Data Tagging

FIG. 4B illustrates a data format diagram including an example of a format 410 for tagging of data consumed by a content suggestion engine 102. As illustrated, the format 410 defines a series of tags (difficulty 414, duration 416, behavior change 418, and restrictions 420) for a set of action statements 406. For example, the action statement 406 "Walk in the Park" may be tagged with a tag for difficulty 414 of "Low"; for duration 416 of "15 Minutes"; for behavior change 418 of "Group"; and for restrictions 420 of "Mobility." FIG. 4B further illustrates the application of these tags for other action statements such as "Eat Oatmeal Breakfast," "40 Minute Rollerblade"; and "Eat Whole Grain Cereal."

A pre-statement 404, post-statement 408, or action statement 406 can be tagged. The action statement 406 can be created by writing, finding, or otherwise defining relevant actions. For example, to pursue actions relevant to weight loss, actions relevant to exercise may include walking, jogging, running, soccer, hockey, tennis, gardening, yard work, swimming, rollerblading, basketball, football, Frisbee®, weight lifting, stairs, jump roping, kickboxing, ZUMBA®, biking, yoga, Pilates, dancing, bowling, volleyball, racquetball, rowing, softball, baseball, skating, skiing, tubing, eating, snowboarding, water boarding, boxing, taking pictures, or writing, and the like. Action statement tags relevant to weight loss may be directed to tags such as eating, movement, self-view, behavior change category, personality type, difficulty, time duration, timeliness, lifestyle, restrictions or limitations, or combinations thereof. If an action or statement could be relevant to more than one of these areas, the action or statement may be tagged with all relevant areas.

The action statement 406 can be personalized, such as by choosing a pre-statement 404 or a post-statement 408, from pre-drafted or templates of pre-statements 404 or post-statements 408. The pre-statement 404 or post-statement 408 can be combined with the action statement 406. The resulting suggested action message 402 can be edited into engaging, appropriate, and coherent language, such as by editing the pre-statement 404 or post-statement 408 to include reference to the action statement 406, to make it unique to the action statement 406, or by adding an explanation of the action, such as by adding a picture or video to help describe the action statement 406. The explanation or a link thereto can be stored along with the suggested action message 402 in a suggested action database 1704 (as referenced in FIG. 17).

In some examples, a behavior change tag can include an individual's intrinsic/extrinsic motivation, such as for suggested actions intended to help the client 106 engage in the activity of the suggested action; individual aptitude, such as for a suggested action intended to help improve knowledge, skills, and strengths to do the activity; group factors, such as for suggested actions intended to have other people (e.g., a supporter from the supporter network 104) encourage the client 106 to perform the suggested action or refrain from a deleterious behavior; group power for causing behavior change, such as for suggested actions intended to provide help, information, or other resources, occurring at a particular time; environmental factors, such as for suggested actions intended to provide a reward, promotion, perk, or cost, such as to encourage the suggested action or discourage deleterious action; environmental power for causing behavior change, such as for a suggested action intended to help the client 106 stay on course; or combinations thereof. A balanced set of actions from many of the behavior change areas can improve the probability of the client 106 meeting their goal(s) 204. The system can promote this balanced set of actions by tracking the behavior change areas chosen, and providing a suggested action message 402 including a tag from those behavior change areas that have been performed less often by the client 106.

In some examples, a psychological assessment tag can be associated with a pre-statement 404, action statement 406, or post-statement 408, such as to match a personality type 210 to the respective statement. The personality type 210 may be used in many settings to extensively customize the content to the client's particular personality.

In some examples, a difficulty tag (e.g., for difficulty 414) can be associated with a pre-statement 404, action statement 406, or post-statement 408, such as to indicate how hard the task is to complete, or to associate a pre-statement 404 or post-statement 408 to an action statement 406 of corresponding difficulty. The difficulty tag can indicate whether the suggested action is easy to execute (e.g., beginner or low difficulty) or that the suggested action does not take a lot of resources (e.g., time, money, or expertise to execute); involves some difficulty (e.g., medium difficulty) in executing (e.g., capability of the human) or that the action requires some resources to execute; or whether the suggested action is difficult (e.g., high difficulty) to execute (e.g., expert input) or requires a significant amount of resources.

A lifestyle tag can include typical times for actions to be presented, such as suggesting breakfast in the morning, or if the client 106 indicates he or she tends to wake up at a certain time, then suggesting breakfast shortly after client 106 wakes up.

A quality check of at least part of the suggested action message 402 (e.g., combination of pre-statement 404, action statement 406, or post-statement 408) can be performed before the suggested action message 402 is delivered to the client 106 (or supporters, as applicable). The pre-statement 404 can be a short message that references an action statement 406 and provides the action statement 406 with a psychological match. The pre-statement 404 and post-statement 408 can be matched, such as to be used together with an action statement 406. The pre-statement 404, post-statement 408, or action statement 406 can be edited for length or sentence structure, such as to be coherent or include less than or equal to a certain number of characters, such as 140 characters (for example, for delivery by short message service (SMS), Twitter, or other messaging services). The edited statements can be recorded in a database (e.g., the suggested action database 1710 illustrated in FIG. 17) as templates for use in future statements.

Other possible types of tags can include motivational, prompt, greeting, reward, or combinations thereof. A message (e.g., a suggested action message 402) can be tagged as a message to a supporter, such as for suggested actions that are intended to promote a supporter to engage the client 106.

Like an action statement 406 or suggested action message 402, a playlist can include a name, keyword, description, or timing constraints. Reminders can be created to let the client 106 know that the suggested action message 402 in a playlist will expire in a specified amount of time. The system can include rules, such as in a rules database 1704 (as described with reference to FIG. 17), for how many playlists can be running at a time, such as no more than three playlists can be running at any given time for the same client 106. The playlist can be presented to the client 106 in a manner similar to how a suggested action is presented.

A client 106 can choose a program with specific keywords or descriptions, such as a keyword or description that is provided with a suggested action or playlist. This can help the system match a particular client already using other programs with a suggested action appropriate to that program or particular client. This can also help professional supporters set up a program for the client 106 to follow. For example, if the client 106 chooses a program for following a Mayo Clinic-approved diet, the suggestion engine 102 can provide a suggested action message 402 or playlists to the client 106 with "Mayo" in the associated keyword or description. The program can have a name, keywords, or description—similar to the action statement 406. The description can include the timing of the playlist. Each action in a playlist can expire in a specified amount of time. Reminders can be created to let the client 106 know that the suggested action message 402 in a program will expire. Rules for how many programs can be running at the same time can be defined, such as a maximum of three programs that can be run for a client 106. Delivery of the program to the client 106 can be similar to delivery of a suggested action. Programs can be approved by a system user, such as a system administrator, prior to allowing the client 106 access to the program.

As a more detailed example of tagging, suggested content may be tagged with one or more tags to indicate various attributes of content and content items. For example, a set of textual characters, a code, or other identifier may be associated with particular attributes for application to content items. A single tag may be associated with a plurality of content items, establishing a one-to-many relationship.

As an example of the application of a tag that indicates "Timeliness", and designates that a tag should be sent during a specific time during the day, the following tags may be applied:

TABLE 1

"Timeliness" Tags

| Timeframe | Tag |
| --- | --- |
| First thing in the morning (breakfast, getting up, etc.) | MOR |
| Noon time (lunchtime, etc.) | NOO |

TABLE 1-continued

"Timeliness" Tags

| Timeframe | Tag |
| --- | --- |
| Early afternoon (2-4PM) | EAF |
| Evening (dinner time, etc.) | EVE |
| Right before bedtime | RBB |

As an example of the application of a tag that indicates "Physical Restrictions," the following indicates restrictions to designate, in which activity the human client should not be engaging in, and what food can the human client not eat. For example, if the client 106 cannot or should not be engaging in activity per a doctor's order, the following tags may be applied. (Restrictions may be applied on a temporary or permanent basis).

TABLE 2

"Physical Restrictions" Tags

| Type of Restriction | Tag |
| --- | --- |
| Weight-bearing on hips, knees or ankles | WBLE |
| Weight-bearing on arms, elbows, wrists, fingers | WBUE |
| Milk allergy | MA |
| Citrus allergy | CA |
| Egg allergy | EA |
| Peanut allergy | PA |
| Tree nut allergy | TA |
| Shellfish allergy | SA |
| Wheat allergy | WA |
| Soy allergy | SYA |
| Gluten Allergy | GA |
| Vegetarian | V |
| Kosher | K |
| Halaal | H |

As another example, a tag may be applied to multiple sets of data points and data values. For example, in categories of poor self-image detected for a client, multiple detected problems may stem from a common tag:

TABLE 3

Tags Applied to Multiple Content Items

| | | |
| --- | --- | --- |
| Low self esteem | SVSE | Poor body image-not toned enough<br>Poor body image-too much fat |
| Poor self-talk | SVST | Negative self-talk that focuses on flaws, mistakes<br>Negative self-talk that focuses on not being able to do something or achieve a goal |
| Lack of accurate perception of self | SVP | Perceiving they are more overweight than they actually are |
| Fear | SVF | Fear of failing<br>Fear of succeeding<br>Fear of looking foolish or silly |
| Unsupportive conversations (family, social) | SVUC | Conversations with family and friends around not being able to lose weight<br>Conversations with family and friends around the benefits about the status quo |
| Lack of integrity | SVI | Lack of follow through<br>Not truly committing to an action |
| Lack of action | SVA | Lazy<br>Competing priorities |

Another example of tagging that may be applied as a psychological attribute is a "behavior change" tag. Behavior change tags may be applied to identify suggestion action items that improve an individual's motivation and aptitude, group factors and power, and environmental factors and power to help change their behavior. In one example, six behavior change areas corresponding to personality types and psychological profiles are defined and applied as tags to various content:

| | |
|---|---|
| Individual's intrinsic/extrinsic Motivation | Find ways to have them want to engage in the activity |
| Individual Aptitude | Have them improve the knowledge, skills, and strengths to do the right thing even when it is hardest. |
| Group factors to behavior change | Have other people (supporters) encouraging the right behavior and discouraging the wrong behavior |
| Group power to cause behavior change | Have others provide the help, information, and resource required at particular times |
| Environmental factors causing behavior change | Make rewards, promotions, perks, or costs encouraging the right behaviors and discouraging the wrong behaviors |
| Environmental power to cause behavior change | Make sure there are enough cues to stay on course. Have the environment (tools, facilities, information, reports, proximity to others, policies) enable the right behaviors and discourage the wrong behaviors |

Application of each of these areas as tags to suggested action content enables customization in a context-sensitive fashion. For example, the use of certain types of suggested actions tagged with an "individual aptitude" tag may be appropriate to a human subject at one point in time; whereas suggested actions tagged with a "group factors" or "environmental factors" tag may be more appropriate to the human subject at other times. A psychological profile of the client 106 (which may be adapted over time) may also indicate the types and amounts of usage of the various categories.

The theory behind this behavior change model states that these areas improve the probability of a human subject making the desired behavior change. These tags may accordingly be used on action statements provided by the content suggestion engine 102. The content suggestion engine 102 will be able to track the clients' use of the action statements in each of the areas and preferentially suggest actions that have many areas included.

These behavior change tag types corresponding to personality profiles may also be used to directly affect the type, format, and result of pre-statements 404, action statements 406, and post-statements 408. In one example, the communication style may be provided from a variety of customized profiles, such as Caregiver, Colleague, Competitor, Authoritarian, and the like, to tailor the content of a suggested action message 402.

TABLE 4

Suggested Action Messages by Communication Style

| Pre-statements | Action statement | Post-statement |
|---|---|---|
| Communication Style: Caregiver | | |
| This is you being really healthy: It's time for your "medicine." Your healthy actions are ready: Ready (or not), This is your caregiver (name) coming to you live . . . | You are going to the park today to take some pictures- | This is what healthy looks like. You'll feel great after. You'll have a great time. You can do this. We're sure it's going to be great. |

TABLE 4-continued

Suggested Action Messages by Communication Style

| Pre-statements | Action statement | Post-statement |
|---|---|---|
| Communication Style: Colleague | | |
| Time for you to get going, Hey, it's time for Woohoo, it's time for: | You are going to the park today to take some pictures- | We're all in this together. Every time you do this it's one more step to being healthy. We're rooting for you. |
| Communication Style: Competitor | | |
| Your teammates and supporters are watching . . . We need you. Are going to let all those youngsters beat you? Wow, are you going to look good today . . . You need some kudos Mary. | You are going to the park today to take some pictures- | You can't win if you don't try You'll have the best day of anyone this week. You'll be the best looking there. On your marks, get set, go. |
| Communication Style: Authoritarian | | |
| Off your duff lady. It is time for some action . . . Get ready for your activity Mary. You signed up for this. Let's get moving. Come on Mary. Time to get going | You are going to the park today to take some pictures | We'll check in after you get back. Remember, do what you say. You can let me know how it went later. Go go go! You can do it, so do it. |

A Tagger may be a human content expert charged with adding, editing, and maintaining content within the content suggestion system. A Tagger must be knowledgeable of the Content Tagging Methodology in order to ensure a high level of quality control and consistency, as well as have sufficient knowledge of the Intervention Model in order to make accurate tagging decisions.

A Tagger may have been trained in understanding each of the following seven tag areas: Lifestyle/problems, Likes/Dislikes, "behavior change" categories, Difficulty, Time duration, Timeliness, and Restrictions. A Tagger uses the psychology of the "behavior change" model, personality types, and coaching styles to define the tags.

A Tagger may tag a suggested action for lifestyle/problems by reading the suggested action and determining whether a person performing that action will receive a benefit to a specific problem category. The following is an example of a self-view suggested action (SV): "Have good posture today! Stand up straight, keep your head up, and make eye contact. Feel the positivity radiate off of you!" This suggested action may benefit two self-view sub-categories: poor self-talk, which has the tag "SVST," and fear, which has the tag "SVF." This suggested action may benefit the specific sub-sub-categories of Poor self-talk, which focuses on flaws, mistakes (SVST1), and fear of failing (SVF1).

The tagging process for a suggested action may include several steps. First, a Tagger may determine if the suggested action will affect each of the problem areas (Movement, Eating, Self-View) using the process of elimination. In the example above, a trained Tagger will agree that the suggested action does not affect the areas of Movement nor Eating.

Next, for each of the affected areas, a Tagger may determine if the suggested action will affect any of the sub-problem areas. In the example above, the process of elimination leaves poor self-talk and fear as the only areas potentially affected.

Next, for each of the sub-problem areas remaining, a Tagger may use the process of elimination yet again to determine the specific sub-sub-problem area. In the example above, the only sub-sub-problem areas affected are negative self-talk, which focuses on flaws and mistakes, and fear of failing (SVST1 and SVF1).

After a Tagger has completed tagging suggested actions, a tagging quality-assurance person may ensure consistency before the suggested actions are included in the useable suggestion database.

Suggestion Engine Operation with Tags

The suggestion engine 102 operates to determine what type of suggestion content (e.g., pre-statement, action statement, post-statement, or combinations thereof) can be chosen for presentation through the supporter network 104 or to the client 106. The suggestion engine 102 can determine what content is appropriate based on questions that the client 106 answers or a set of rules that can be applied to both restrict and narrow content, such as by weighting and filtering the suggested actions.

FIG. 5 illustrates a grid 500 depicting relationships between example content (actions 502) and tag categories (tags 504) according to an example described herein. For example, a particular action such as "Stay hydrated in between meals today" may be associated with one or more particular behavior change categories, keywords, attributes, categorizations, and tag values. Further, depicted in the grid 500 are other examples of actions and associated tag values.

As depicted in grid 500, the tag categories may include: Lifestyle Category (Eating, Movement, Self-View); Sub Problem Category; Sub-Sub Problem Category; Likes/Dislikes; Custom Attributes; Difficulty; Time Duration. Content items (actions 502) which satisfy one or more of these categories will be tagged accordingly. For example, behavior change attributes (attributes 1 through 6) may be defined to include: Personal Ability; Personal Motivation; Social Ability; Social Motivation; Structural Ability; Structural Motivation.

As non-limiting examples of additional tag types and tag categories, the following section outlines tags that may be deployed for the categorization of behavior-related content.

Interest Tags

There may be any number of tag types that may be used to describe the interests of an exemplary client, who would most likely respond positively to the content and find the content effective. As illustrative examples, these tags may include:

Area of Activity

The possible values for this tag may be "Urban," "Suburban," and "Rural."

Outdoors

The possible values for this tag may be "Low," "Moderate," and "High."

Religiosity

The possible values for this tag may be "Low," "Moderate," and "High."

Spirituality

The possible values for this tag may be "Low," "Moderate," and "High."

Sweet Foods

The possible values for this tag may be "Low," "Moderate," and "High."

Animal-based Food Products

The possible values for this tag may be "Low," "Moderate," and "High."

Pets

The possible values for this tag may be "Low," "Moderate," and "High."

Time of Day

The possible values for this tag may be "Morning," "Midday," "Afternoon," "Evening," and "Nighttime."

Ability Tags

There may be 10 tag types that may be used to describe the ability of an exemplary client, who would respond positively to the content and experience a successful outcome. They are:

Cognitive

The possible values for this tag may be "Low," "Moderate," and "High."

Age

The possible values for this tag may be "Young," "Middle-aged," and "Elderly."

Income

The possible values for this tag may be "Low," "Moderate," and "High."

Overall Health Status

The possible values for this tag may be "Low," "Moderate," and "High."

Readiness for Change

The possible values for this tag may be "Low," "Moderate," and "High."

Motivation

The possible values for this tag may be "Low," "Moderate," and "High."

Raw Physical Ability

The possible values for this tag may be "Low," "Moderate," and "High."

Raw Structural Ability

The possible values for this tag may be "Low," "Moderate," and "High."

Raw Self-View

The possible values for this tag may be "Low," "Moderate," and "High."

Raw Social Ability

The possible values for this tag may be "Low," "Moderate," and "High."

Member State Tags

There may be three tag types used to describe an exemplary client's state prior to being exposed to the content. They are:

Point in Weight Loss Process

The possible values for this tag may be "Early," "Moderate," and "Late."

Past Weight Loss Attempts

The possible values for this tag may be "None," "Some," and "Many."

Current Program Subscriptions

The possible values for this tag may be "None," "Some," and "Many."

Challenge Tags

There may be five tag types that describe potential challenges that must be overcome by an exemplary client in order to increase the likelihood of a positive response to the content by the client. They are:

Structural

The possible values for this tag may be "Low," "Moderate," and "High."

Current Eating Habits

The possible values for this tag may be "Poor," "Fair," and "Excellent."

Current Fitness Habits

The possible values for this tag may be "Poor," "Fair," and "Excellent."

Mood

The possible values for this tag may be "Poor," "Fair," and "Excellent."

Well-Being

The possible values for this tag may be "Poor," "Fair," and "Excellent."

Constraint Tags

There may be six tag types that describe constraints, or requirements, that must be met or exceeded by an exemplary client in order to increase the likelihood of a positive response to the content by the client. They are:

Physical Activity

The possible values for this tag may be "Low," "Moderate," and "High."

Difficulty

The possible values for this tag may be "Low," "Moderate," and "High."

Economic

The possible values for this tag may be "Low," "Moderate," and "High."

Duration

The possible values for this tag may be "Low," "Moderate," and "High."

Season

The possible values for this tag may be "Spring," "Summer," "Fall," and "Winter."

Food Allergy

The possible values for this tag may be "Low," "Moderate," and "High."

Tagging Model

The operations of the Content Suggestion Engine may be facilitated by a tagging model in accordance with the techniques described herein. The suggestion is tagged with one or more keywords in order to be processed by the suggestion engine. The appropriate suggestion may then be retrieved based on the keyword tags.

Consider the example of the following suggestion: "Have an omelet for breakfast today." This suggestion is tagged with keyword tags representing "Egg" and "Breakfast." Suppose the Client has indicated a like of eggs in her profile. This suggestion will be available for the suggestion engine to apply the weightage to favor/prefer this suggestion. The more the weightage is, the more suitable the suggestion is for the client (assuming this suggestion passes through the filter process).

The suggestion engine may apply different scores based on the tags. For example, the suggestion engine may add a "+1" score with every tag that matches with the profile, and subtract a "−1" score when the tag of the suggestion matches some restriction (such as an allergy) or a dislike of the user's profile. Because this suggestion tag "Egg" and "Breakfast" matches with user's profile, an increased score of +2 will be given to this suggestion.

If other users in the past have completed this suggestion a certain number of times, say five times, and all given positive points to the difficulty, timeliness, and helpfulness levels, the suggestion is also more likely to be selected. The system keeps the average of total ratings and adds to the score, to give this suggestion more weightage for this user. This process is a self-learning process that may use crowdsourcing combined with profile metrics to better align the right suggestion with the right user. Thus, the system over time improves through a dynamic process, increasing the chances that the more appropriate suggestion is delivered to the user than a suggestion less appropriate for the user.

Another example of tags are the specific tags for eating, movement and self-view suggestions, for example, a "MTR1" tag will be used for the suggestion that will be helpful for the clients who have indicated they have a work schedule that makes it difficult to set time for exercise. Those tags again will be matched against the profile, so if the user has indicated a difficulty to exercise because of a work schedule in his or her user profile, then +1 will be added to this suggestion. These tags are the structured tags that provide generic and literal context when applied to a suggestion. The tags help classify in quick succession the categorization for a particular suggestion. In some cases, the tags also provide additional context, but is the free flowing tags that may be used to provide a more subtle description to a suggestion.

Because user profile data is structured and or can be unstructured (for example: likes and dislike are structured, but a real-time measure of weather is variable and unstructured), free-flowing tags may allow a qualifying tag for a suggestion to provide greater granularity. Thus, free-flowing tags also provide a suggestion with enhanced context and application to a user and his or her real-time metrics. Real-time metrics can be values such as a current state of the user's environment, conditions, or any other variable that has contextual value to a suggestion and the user.

There are certain tags that may assist the suggestion engine to make certain decisions, and those tags may be predefined in the system. For example, a MISC_NO_DESTINATION tag may be used for a suggestion that needs to be given for the user when her destination is not set. Such tags are system tags and would assist a user's onboarding process.

Thus, tags can be structured or unstructured. The self-learning component of a crowd-sourcing feedback loop all combine to provide a higher level of context to a suggestion. A suggestion on its own does not provide value. It is through the tagging process and the feedback loop that the suggestion engine is able to qualify its efficacy for a particular user at a particular time around a particular variable environment.

Usage of Tagging Content in the Suggestion Engine

Figure 6A:
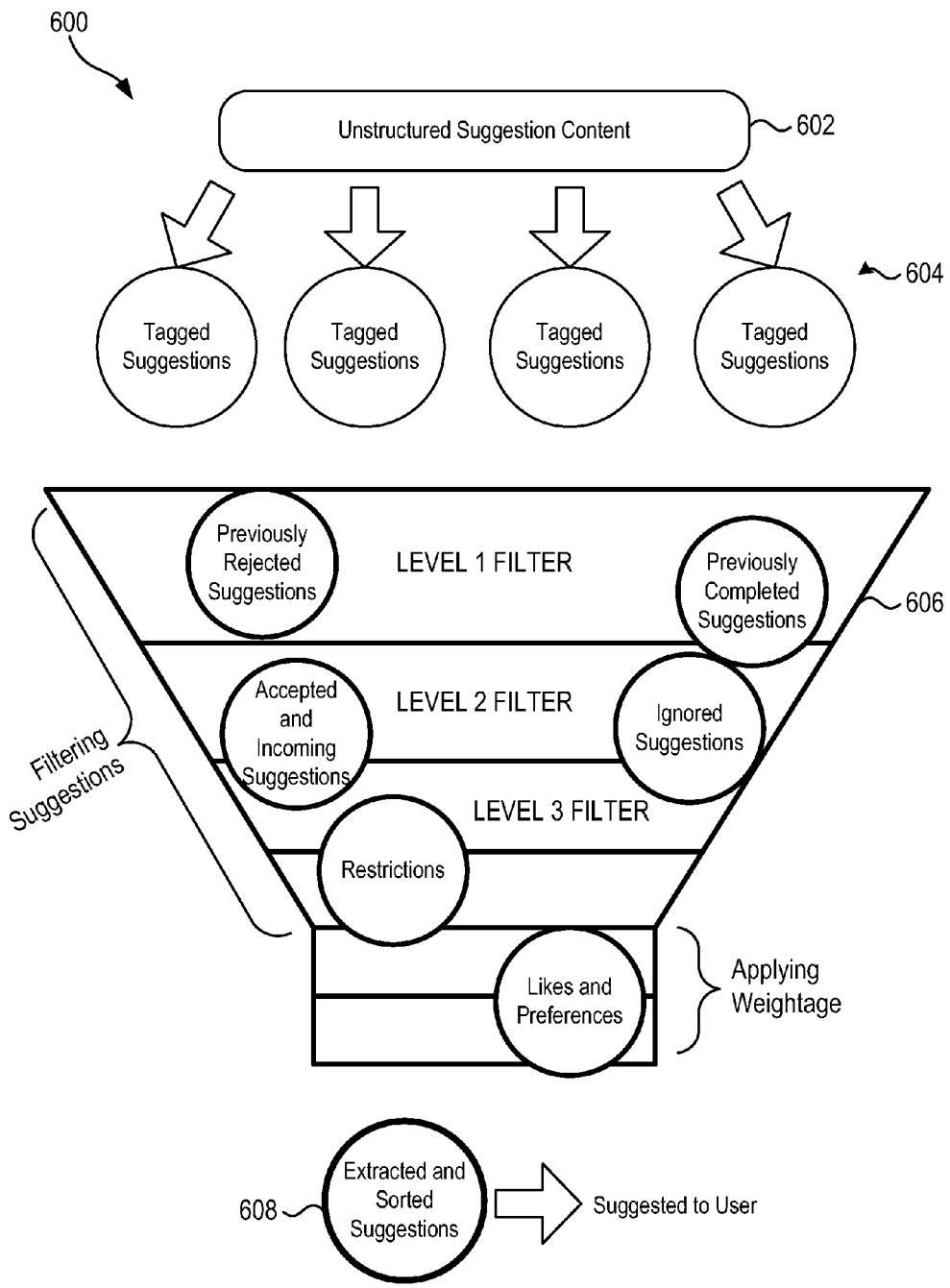
FIG. 6A illustrates a process of using tagged suggestion content in connection with a filtering and weighing process 600 by a content suggestion engine according to an example described herein.

FIG. 6A provides an illustration of using tagged suggestion content in connection with a filtering and weighing process 600 according to one example. As shown, input data in the form of unstructured suggestion content 602 is transformed into tagged suggestions 604 upon association with tags.

In this example, the content suggestion engine applies a series of filters and weights 606 based on tag values determined from the user's profile, taking into consideration the user's likes and dislikes, allergies, lifestyle and other preferences, to the tagged suggestions 604. These filters and weights are used to apply the tagging model, to exclude or emphasize particular suggestions based on their associated tags, and extract the most appropriate suggestions for the user 608.

After going through the profile of the user, the suggestion engine may read the destination set by the user to identify the number of suggestions required in a week. For example: if the user has decided to opt for three eating-based, five activities-based and two self-based suggestions in a week, the suggestion engine will take into account these destinations and offer the appropriate amount of self-based, eating-based and activity-based suggestions.

The suggestion engine uses a filtering process to extract the best possible suggestion for the user based on their profile and goal. The filtration process includes the removal of suggestions that were rejected by the user; these suggestions if discarded once may remain rejected forever. The filtration process then goes on to reduce the suggestions that were skipped by the user. The skipped suggestion will not be taken into consideration for a period of time, such as the next seven days. After this, the filtration process removes those suggestions that the user has already completed in a period of time, such as the last six months, and disregards the suggestions that are already available in the user's incoming suggestion bucket.

The next step of filtration will be applied to filter out the suggestions based on restrictions such as user allergies and the items marked as disliked by the user. For example, if one of the suggestions includes consuming a glass of milk and the user has defined in his or her profile that he/she is allergic to milk, such suggestions are removed.

After the filtering is applied, the suggestion engine then applies the weightage to the suggestions based on the tagging model. Because each suggestion is tagged to provide a context to the suggestion, the tags can be used to match the tag with the tags from the profile of the user. Thus, the closer that the tag values matches to the user's profile, the more weight that is given to that particular suggestion.

The next step of applying weightage is based on the difficulty, timeliness and helpfulness levels. The suggestion engine takes into consideration these factors and sorts out the suggestions. For example: the suggestion engine goes though the difficulty, timeliness and helpfulness levels of suggestions which the user has rated in his or her profile, and evaluates this information into considerations to sorts out suggestions which are more or less of interest to a user.

Once the suggestions are sorted, the suggestion engine extracts the top weighted suggestions that are the best interest of the user for the particular goal or destination. At this time, the extracted and sorted suggestions are provided to the user by the suggestion engine.

Figure 6B:
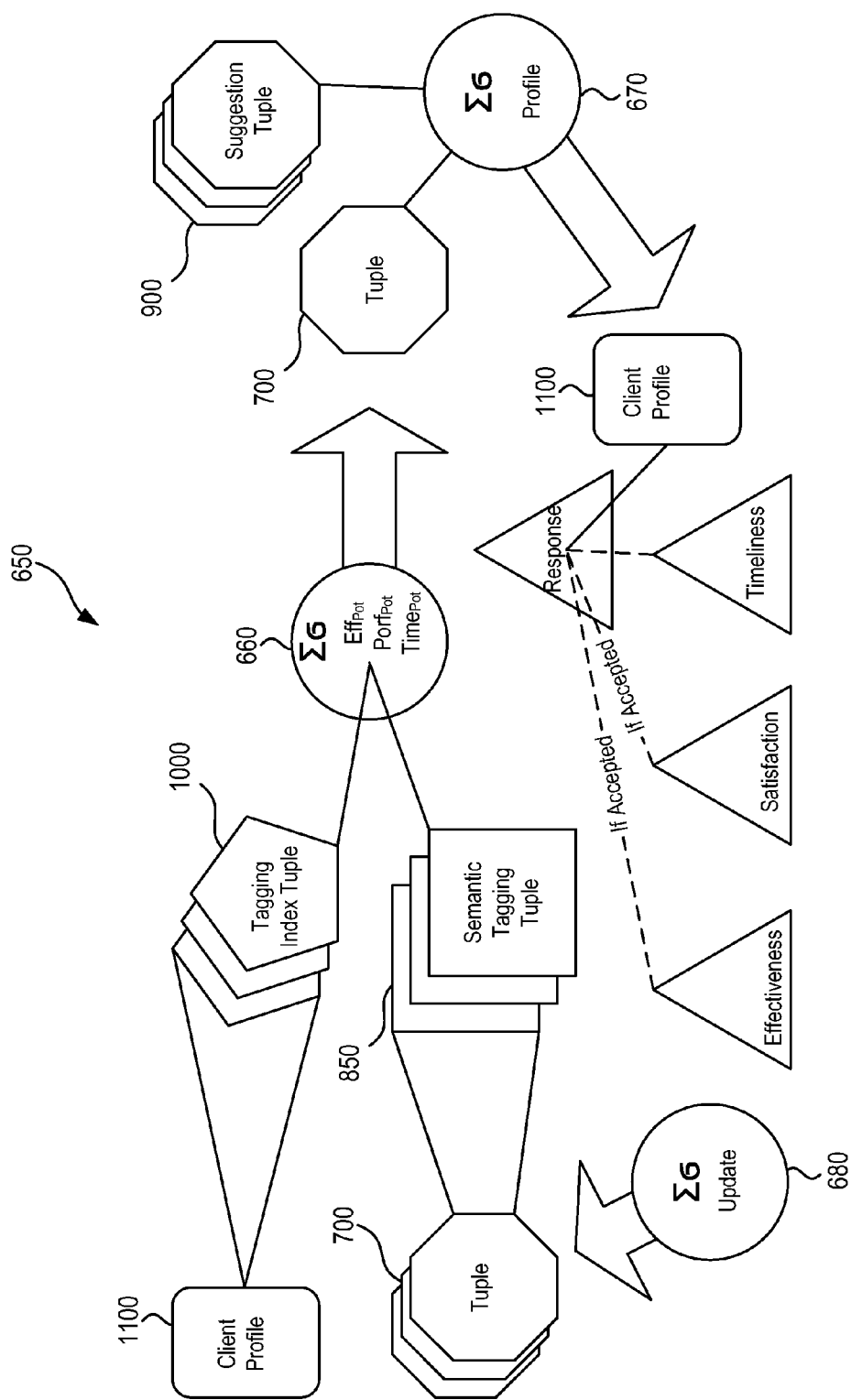
FIG. 6B illustrates a process of entering, tagging, storing, and managing content by a content suggestion engine according to an example described herein.

FIG. 6B illustrates a process 650 of entering, tagging, storing, and managing content by for use with a content suggestion engine according to an example described herein. As illustrated, the process includes a number of relationships between operations and data structures, including data structures further described herein. The data structures specifically identified in the process 650 include a Content Suggestion Tuple 700, a Semantic Tagging Tuple 850, a Suggestion Tuple 900, a Tagging Index Tuple 1000, and a Client Profile 1100.

As illustrated, relationships between the Content Suggestion Tuple 700 and a Semantic Tagging Tuple 850, and relationships between a Client Profile 1100 and a Tagging Index Tuple 1000, are used in connection with a function 660. The results of this function 660 provide updates to the Content Suggestion Tuple 700.

The Content Suggestion Tuple 700 and the Suggestion Tuple 900 provide specific input to a profile function 670. From the profile function 670, updates to the Client Profile 1100 include attributes of response, timeliness, satisfaction (if accepted) and effectiveness (if accepted). Additionally, an update function 680 may be used to provide updates to the Content Suggestion Tuple 700.

Data Tagging Structures

A variety of data structures may be used in connection with the tagging functionalities described here. The following examples in FIG. 7-FIG. 13 illustrate detailed data structures used to maintain and store tags for a particular database schema and setup. It will be understood that other database values and configurations may be maintained and utilized for tagging functions.

Figure 7:
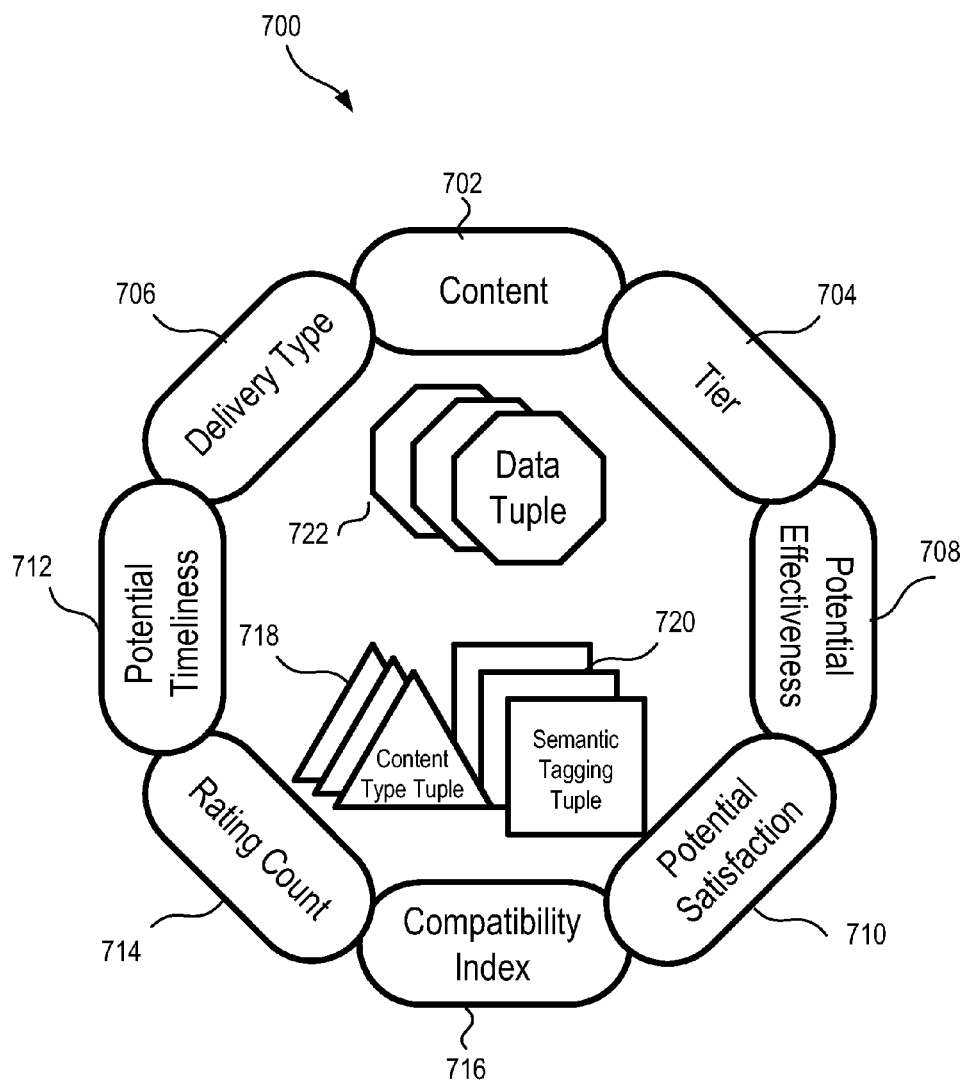
FIG. 7 illustrates a Content Suggestion Tuple data structure for encapsulating a candidate piece of content to be considered as a suggestion to a client according to an example described herein.

FIG. 7 illustrates a Content Suggestion Tuple 700 data structure for encapsulating a candidate piece of content to be considered as a suggestion to a client 106, according to an example described herein. The Content Suggestion Tuple 700 may be an 8-tuple (an "octuple") containing the following components:

(1) Content 702—Depending on the medium of the content, this component either may contain the actual text of the suggestion or may contain a URL to the actual content. For example, if the suggestion format is text messaging or email, the content 702 may contain the actual text of the suggestion; if the suggestion format is media, the content 702 may contain a URL to the content. Content 702 may be uniquely identified by a Content ID.

A Content ID may be a machine-generated unique identity (usually a static, non-repeating, positive integer) of the actual content record located in the content management system. In some embodiments, once a piece of content has been released into production, it cannot be modified; to "edit" the content a copy of the content is made, a new Content ID is generated, and modifications are made to the new copy. In addition, a reference to the original parent content record may be maintained. In this way, new modifications can benefit at least partially from what was learned about parent content (ostensibly similar) regarding ratings, while the integrity of the association between content and ratings is maintained.

(2) Tier 704—The tier 704 indicates the level of content represented by the Content Suggestion Tuple 700. Tiers 704 may be used by the content suggestion engine 102 during the iterative, interactive suggestion process. As the suggestion engine 102 begins formulating a list of suggestions for a client 106 or supporter in supporter network 104, the suggestion engine 102 may begin with general actions. If an action is accepted, the suggestion engine 102 may then construct a list of suggestions that are more specific to the selected action. These secondary or second-tier suggestions may include, for example, support messages. Generally, the suggestion process may take a hierarchical approach in that lower-tiered suggestions will not be delivered until the related higher-tiered suggestion is first accepted by the client 106 or a supporter in the supporter network 104. However, a particular response to a prompt may drive another support message.

The highest tier 704 may be the "general' tier 704, which may indicate a suggestion to take a general action, such as "Do exercises each day for a week," or the like.

The second-highest tier 704 may be the "specific" tier 704, which may indicate a more specific suggestion, such as "Go inline-skating in the park," or the like. Suggestions in the "specific" tier 704 may be driven by a positive response to a prior "general" suggestion.

The third-highest tier 704 may be the "support" tier 704; content in this tier may be messages offering support, such as "Inline-skating lets you enjoy the weather and work toward your goals. You can do it! Keep on trucking!" A message in this tier 704 may be delivered to the client 106 after the client 106 has accepted "specific" suggestion associated with the message.

The fourth-highest tier 704 may be the "prompt" tier 704; content in this tier 704 may be follow-up messages prompting the client 106 to provide status information regarding the specific action selected. An example message in this tier 704 may be "On Tuesday, you decided to go inline-skating in the park for 20 minutes each day. How many times have you done so?"

(3) Delivery Type 706—Content 702 may be delivered to a client 106 or a supporter in the supporter network 104 in a number of different ways (e.g. email, SMS, Adobe Flash movie, MP3, etc.) The Delivery Types 706 may contain a value (or values) that represent(s) the appropriate delivery types for the content 702; the value may be encoded as a bit field, a set of flags, or another suitable data structure that facilitates representing multiple types of delivery. A Tagger may be responsible for selecting each delivery type that may be appropriate for each piece of content 702.

For example, the Delivery Types 706 may contain a value encoded as a binary bit field with the following delivery types:
- 0=None
- 1=Email
- 2=SMS
- 4=Facebook
- 8=Twitter
- 16=Flash Player
- 32=MP3 Player By assigning numeric values to each valid delivery type, such that each new type is assigned a value equal to twice the maximum value in the existing list, a means of recording all combinations of delivery types with a single integer value is possible. For example, if a Tagger determines that a given piece of content can most appropriately be delivered via email, SMS, and a Facebook Wall-to-Wall post, selecting these three delivery types will generate an integer value of 1+2+4=7. No other combination of delivery types can generate this value. The decimal value 7 is represented in binary as 000111 (NOTE: since there are six possible delivery types in this example, the first three zeroes are included as placeholders.) Given an encoded value for the Delivery Types 706, it is easy to work back from the encoded value to determine which delivery type(s) was/were selected by simply reversing the order of the types and identifying which delivery types are flagged with a "1". For example, given the encoded value of 26, first convert 26 into binary (011010), then check the selected delivery types with values 16 (Flash Player), 8 (Twitter), and 2 (SMS). To double-check this, add 16+8+2=26.

In some cases, when the suggestion engine 102 is searching for a content suggestion to deliver, the suggestion engine 102 may wish to limit the search space to suggestions with a certain delivery type. In such cases, the suggestion engine 102 may use the value(s) in the Delivery Type 706 of a Content Suggestion Tuple 700 to optimize the suggestion engine's search.

Naturally, content may be delivered in more than one way. For example, text-based content may be delivered via SMS, email, or a Facebook Wall-to-Wall post. However, this does not imply that every possible delivery type is necessarily appropriate for a given piece of content; therefore, a Tagger may decide which delivery type(s) is/are appropriate for a given piece of content.

(4) Potential Effectiveness Rating 708—The "Potential Effectiveness Rating" 708 of the Content Suggestion Tuple 700 may be a calculated value derived from two differently weighted sources. The first source may be a list of similar suggestions previously presented to the user, and the user's corresponding effectiveness ratings of those suggestions (i.e. via Suggestion Tuples, described in FIG. 9). The second source may be the aggregate measure of Potential Effectiveness 708 of the suggestion based on the ratings of similar clients 106.

A prompt for an Effectiveness rating may be scheduled to occur after a client 106 logs in to the system, after a specified time period has elapsed since the suggestion was given, or a combination thereof. The rating may be recorded along with the client's profile tuples (as referenced in FIGS. 11-12), and may be used to calculate the content's potential effectiveness 708 for the current client, e.g., the client 106.

(5) Potential Satisfaction Rating 710—At a time a suggestion is made to a client 106, the client 106 may reject, ignore, or accept a suggestion. The choice may be recorded along with the client profile tuple (as referenced in FIGS. 11-12) and may constitute the primary term in the calculation of the client's current potential preference for the content.

A prompt for a Satisfaction rating may be scheduled to occur after a client 106 logs in to the system, after a specified time period has elapsed since the suggestion was given, or a combination thereof. This rating may also be recorded along with the client's profile tuples (as referenced in FIGS. 11-12), and may constitute the secondary term in the calculation of the client's overall preference for the content.

(6) Potential Timeliness Rating 712—At a time a suggestion is made to a client 106, the client 106 may reject, ignore, or accept the suggestion. When rejecting a suggestion, the client 106 may indicate that the suggestion was untimely delivered. This indicator may be recorded along with the client's profile tuples (as referenced in FIGS. 11-12), and may constitute the primary term in the calculation of the current potential timeliness of the content.

A prompt for a Timeliness rating may be scheduled to occur after a client 106 logs in to the system, after a specified time period has elapsed since the suggestion was given, or a combination thereof. This rating may be recorded along with the client's profile tuples (as referenced in FIGS. 11-12), and may constitute the secondary term in the calculation of the current content's overall timeliness.

(7) Rating Count 714—The Rating Count 714 may be a fuzzy positive numeric value representing the number of ratings of the content that have been made by clients 106 with similar client profiles. A client 106 whose client profile matches the current client's profile exactly may contribute 1.0 to the Rating count 714. A client 106 whose client profile has absolutely no similarity to the current client's profile may contribute 0.0 to the Rating count 714. A client 106 who has some similarity to the current client's profile may contribute a value between 0.0 and 1.0, according to the degree to which their client profile is similar to the current client's profile.

(8) Compatibility Index 716—The Compatibility Index 716 for a suggestion may be determined dynamically based on an aggregate fuzzy calculation of the degrees of similarity between certain components of the client's profile and certain components of the content profile. Content 702 with a high Compatibility Index 716 (e.g., approaching 1.0) might be a better candidate for use in a suggestion for the client 106 than might content with a lower index (i.e., approaching 0.0). Content 702 with a Compatibility Index 716 less than the Compatibility Threshold 856 (as referenced in FIG. 8B) may be excluded from the list of candidates for suggestion.

Figure 8A:
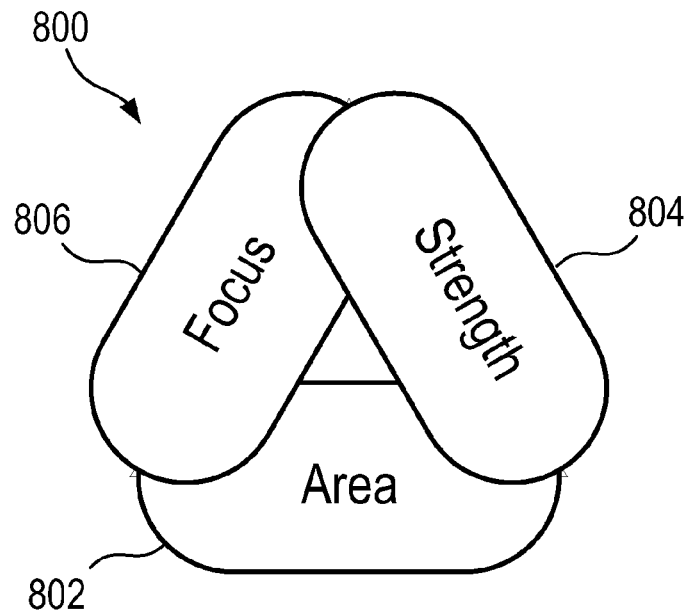
FIG. 8A illustrates a Content Type Tuple data structure for describing a content type of a content suggestion according to an example described herein.

A Content Suggestion Tuple 700 may also contain a listing 718 of one or more Content Type Tuples 800 (as referenced in FIG. 8A). A Content Suggestion Tuple may also contain a listing 720 of one or more Semantic Tagging Tuples 850 (as referenced in FIG. 8B). A Content Suggestion Tuple 700 may also contain a listing 722 of references to one or more Content Suggestion Tuples.

FIG. 8A illustrates a Content Type Tuple 800 data structure for describing a content type of a content suggestion according to an example described herein. The content suggestion engine 102 may search for possible content suggestion candidates by filtering the content suggestions by content type; doing so may provide a cost-effective means for reducing the search space.

Each Content Type tuple 800 may have one value from each of the three dimensions (Area 802, Strength 804, and Focus 806.) The Area dimension 802 can have the following values: Movement, Eating, or Self-View. The Strength dimension 804 can have the following values: Motivation and Aptitude. The Focus dimension 806 can have the following values: Personal, Group, and Environmental. For each unique combination of three dimensions to which a piece of content may be applicable, a Tagger may create a Content Type Tuple 800 containing those values; thus, there may be eighteen different possible Content Type Tuples 800. In some embodiments, there are at least one and no more than eighteen Content Type Tuples 800 associated with a Content Suggestion Tuple 700 in order for the content suggestion to be available to the content suggestion engine 102.

Figure 8B:
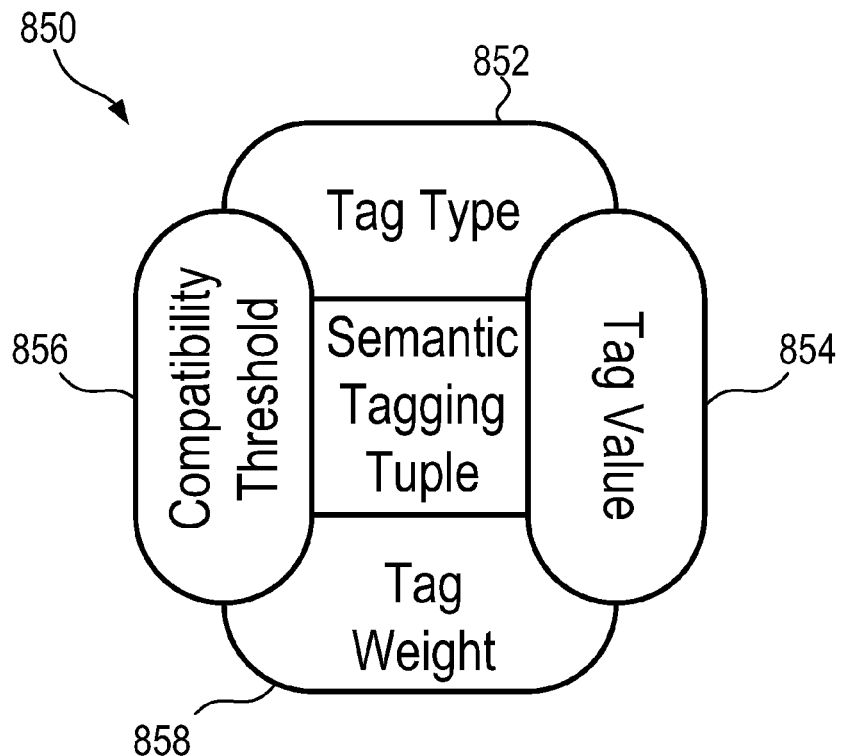
FIG. 8B illustrates a Semantic Tagging Tuple data structure for describing the degree to which a tag is compatible with a client profile according to an example described herein.

FIG. 8B illustrates a Semantic Tagging Tuple 850 data structure for describing the degree to which a tag is compatible with the client's profile and other selection criteria at a time the content suggestion engine 102 selects content, according to an example described herein. Each Semantic Tagging Tuple 850 may contain the following components: (1) Tag Type 852, (2) Tag Value 854, (3) Compatibility Threshold 856, and (4) Calculated Tag Weight 858. With these four components, a Semantic Tagging Tuple 850 may provide the information necessary to calculate the degree to which a suggestion tagged with the Semantic Tagging Tuple 850 is compatible (represented by the Calculated Tag Weight 858) with the client's profile, and other selection criteria, at a time the content suggestion engine 102 selects content. As such, Semantic Tagging Tuples 850 describe both the client 106 and the suggestion.

(1) Tag Type

Within the content management system, a finite number of tags may be maintained. General tag types (maintained with Tag Type 852) may include Duration, Difficulty, Cost, Socialization, etc. Types of Semantic Tagging Tuples 850 may include interests (i.e., area of activity), abilities (i.e., raw physical ability), client state (i.e., progress towards goals), challenges, and constraints (i.e. physical activity). Specific tag types may also be defined for each content type. For example, if there is a content type called "Eating," there may be additional applicable tags such as "Restriction," "Modification," "Schedule," etc.

The tag types may be ordinal, and may be quantifiable on a continuous numeric domain. For example, the Difficulty tag type may be understood to cover a fixed domain (e.g., from "Very Easy" to "Very Difficult.") The semantic value "Very Easy" may have a corresponding numeric value of 0.0, while "Very Difficult" may have a numeric value of 1.0. Between these two extremes of the domain may lie a fixed number of additional semantic values (e.g., "Easy," "Moderate," and "Difficult"), and each may be centered on a numeric value, and may overlap. Overlapping semantic values may be direct counterparts to fuzzy sets.

(2) Tag Value

For each Tag Type 852 there may be a fixed range of overlapping semantic values that cover the tag's entire domain. The Tag Value 854 of the Semantic Tagging Tuple 850 may contain the actual semantic value assigned by a Tagger. This value may be used to determine the tag's Calculated Tag Weight 858.

(3) Compatibility Threshold

The Compatibility Threshold 856 may be a value within the range of 0.0 to 1.0. As the value approaches 1.0, there may be a heavier requirement that the value of this tag be compatible with the value of the corresponding component of the profile for the client 106. When the compatibility falls below this threshold, the Calculated Tag Weight 858 may be determined to be 0.0; otherwise, the Calculated Tag Weight 858 may be equivalent to the compatibility value.

(4) Calculated Tag Weight

The Calculated Tag Weight 858 may be a modified measure of the degree of compatibility between the current Tag and a corresponding component of the profile for the client. If the degree of compatibility falls below the Compatibility Threshold, the Calculated Tag Weight 858 may be set to 0.0; otherwise, the Calculated Tag Weight 858 may be equivalent to the compatibility value.

The Calculated Tag Weight 858 may be a dynamic variable; it may be calculated after a candidate set of suggested content has been queried and dynamically updated. For each of the candidates, the similarity of their tag value to that of the client's Tagging Index Value may be calculated and moderated by the Tagging Index Tuple's 1000 Current Semantic Truth 1010 value (as referenced in FIG. 10).

The list of Semantic Tagging Tuples 850 is created by a Tagger by determining the extent to which each of the available Semantic Tag Types 852 applies to the content.

Figure 9:
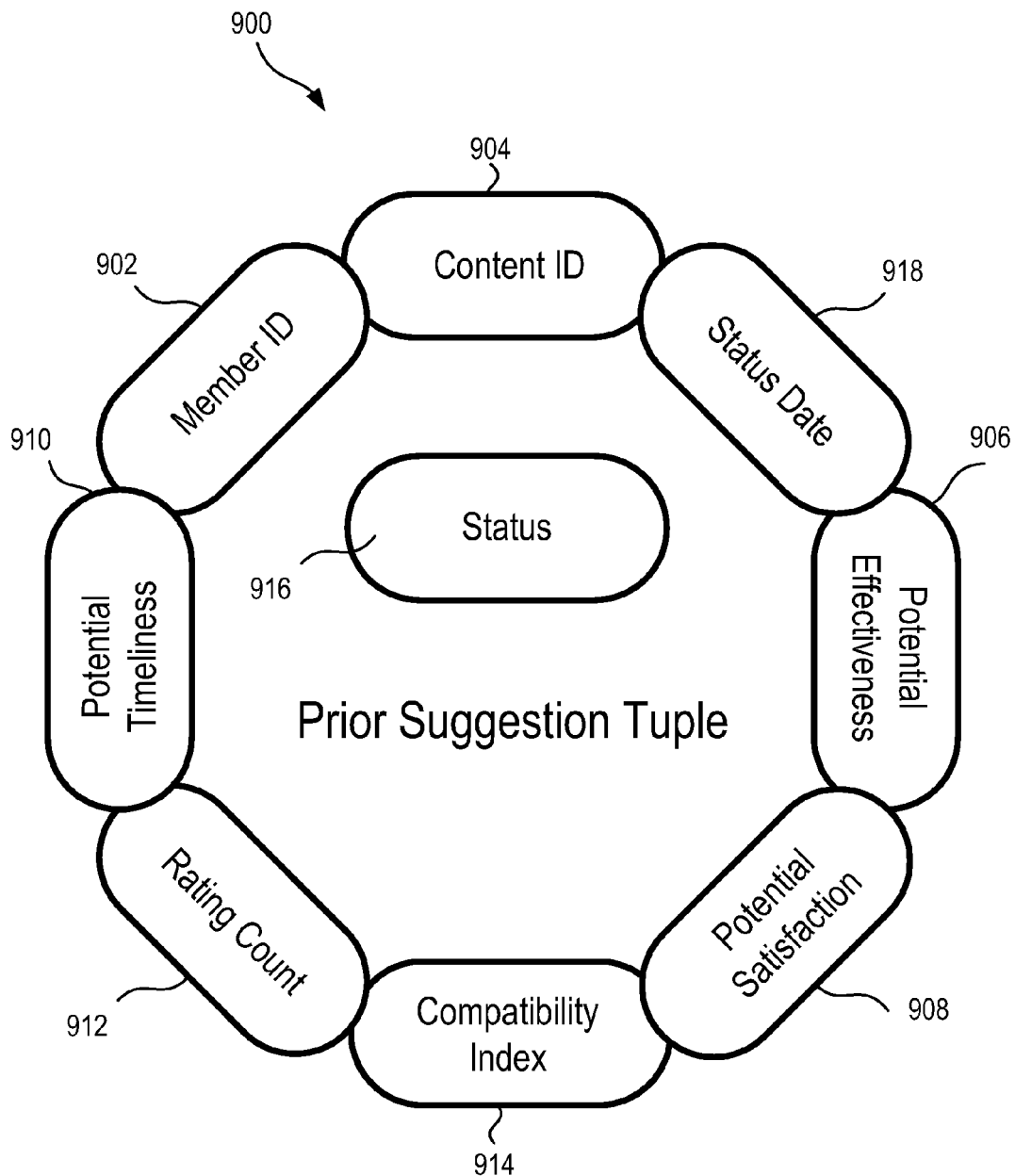
FIG. 9 illustrates a Prior Suggestion Tuple data structure for encapsulating knowledge of prior suggestions according to an example described herein.

FIG. 9 illustrates a Prior Suggestion Tuple 900 data structure for encapsulating temporal knowledge of prior suggestions, according to an example described herein. A Prior Suggestion Tuple 900 may be used to calculate the Potential Effectiveness 708 and Potential Satisfaction 710 ratings of a content suggestion candidate.

A Prior Suggestion Tuple 900 may contain the following components: (1) a Client ID 902, (2) a Content ID 904, (3) a Potential Effectiveness Rating 906 at the Time of Suggestion, (4) a Potential Satisfaction Rating 908 at the Time of Suggestion, (5) a Potential Timeliness Rating 910 at the Time of Suggestion, (6) a Rating Count 912 at the Time of Suggestion, (7) a Compatibility Index 914 at the Time of Suggestion, (8) Status 916, and (9) Status Date 918.

(1) Client ID 902 may be a machine-generated unique identity (usually a static, non-repeating, positive integer) of the actual client record located in the database.

(2) Content ID 904 may be a machine-generated unique identity (usually a static, non-repeating, positive integer) of the actual content record located in the database.

(3) The Potential Effectiveness Rating 906 at the Time of Suggestion captures the Potential Effectiveness 708 of the suggestion, as calculated within the Content Suggestion Tuple 700 (as referenced in FIG. 7) at the time the suggestion was presented to the client 106.

(4) The Potential Satisfaction Rating 908 at the Time of Suggestion captures the Potential Satisfaction 710 of the suggestion, as calculated within the Content Suggestion Tuple 700 (as referenced in FIG. 7) at the time the suggestion was presented to the client 106.

(5) The Potential Timeliness Rating 910 at the Time of Suggestion captures the Potential Timeliness 712 of the suggestion, as calculated within the Content Suggestion Tuple 700 (as referenced in FIG. 7) at the time the suggestion was presented to the client 106.

(6) The Rating Count 912 at the Time of Suggestion captures the Rating Count 714 of the suggestion, as calculated within the Content Suggestion Tuple 700 (as referenced in FIG. 7) at the time the suggestion was presented to the client 106.

(7) The Compatibility Index 914 at the Time of Suggestion captures the Compatibility Index 716 of the suggestion, as calculated within the Content Suggestion Tuple 700 (as referenced in FIG. 7) at the time the suggestion was presented to the client 106.

(8) The Status 916 stores the status of the prior suggestion. There may be six possible Status 916 values for a prior suggestion: "Rejected," "Rejected for Untimeliness," "Ignored," "Accepted and Cancelled," "Accepted and Open," and "Accepted and Completed." The Status 916 may be a static value.

A Prior Suggestion Tuple 900 with a Status 916 of "Rejected" may indicate the suggestion was rejected by the client 106.

A Prior Suggestion Tuple 900 with a Status 916 of "Rejected for Untimeliness" may indicate the suggestion was rejected by the client 106 because the suggestion was delivered at an inopportune or inconvenient time.

A Prior Suggestion Tuple 900 with a Status 916 of "Ignored" may indicate the suggestion was ignored by the client 106.

A Prior Suggestion Tuple 900 with a Status 916 of "Accepted and Cancelled" may indicate the suggestion was initially accepted by the client 106, but the client 106 later cancelled or rejected the suggestion.

A Prior Suggestion Tuple 900 with a Status 916 of "Accepted and Open" may indicate the suggestion was accepted by the client 106, but has not yet been completed by the client 106.

A Prior Suggestion Tuple 900 with a Status 916 of "Accepted and Completed" may indicate the suggestion was accepted by the client 106 and has been completed by the client 106.

(9) The Status Date 918 may store the date and/or time when the Status 916 was set for the suggestion. The Status Date 918 may be a static value.

Figure 10:
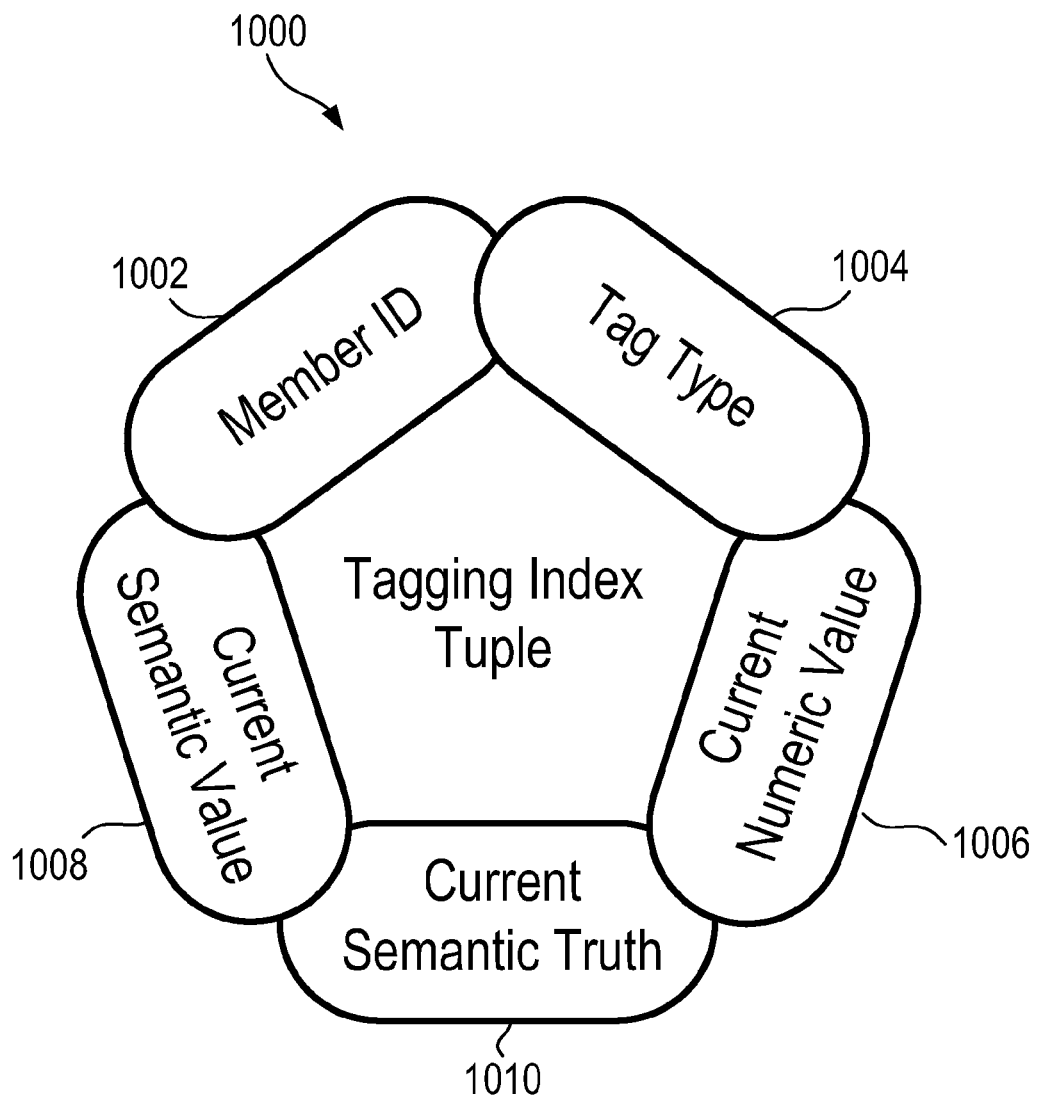
FIG. 10 illustrates a Tagging Index Tuple data structure for representing essential information regarding client characteristics according to an example described herein.

FIG. 10 illustrates a Tagging Index Tuple 1000 data structure for representing essential information regarding a client's characteristics that correspond to a fixed list of general and content-specific tagging types, according to an example described herein. Components of a Tagging Index Tuple 1000 may include: (1) a Client ID 1002 of the client 106, to whom the Tagging Index Tuple 1000 applies, (2) a Tag Type 1004, (3) a Current Numeric Value 1006, (4) a Current Semantic Value 1008, and (5) a Current Semantic Truth Value 1010.

(1) Client ID 1002 may be a machine-generated unique identity (usually a static, non-repeating, positive integer) of the actual client record located in the database.

(2) Tag Type 1004—Within the content management system, a finite number of tags may be maintained. The tag types 1004 may be ordinal, and may be quantifiable on a continuous numeric domain. Tag Type 1004 may be sued to match a client's current profile status with the specified characteristics (i.e., tags) of content. For each tag listed in a Content Suggestion Tuple 700, a corresponding Tagging Index Tuple 1000 may be created and populated with Current Semantic Values 1008. These values may then be used (in collaboration with all the other tags listed in the Content Suggestion Tuple 700) to determine the degree to which the candidate content suggestion is relevant to, and compatible with, the client's current status.

(3) Current Numeric Value 1006 may be captured from the client's current status via an aggregation of current values in the Client Profile 1100 (as referenced in FIG. 11) or via direct prompting for a rating from the client 106. When a Current Semantic Value 1008 is recorded instead of a Current Numeric Value 1006, the Current Numeric Value 1006 may be determined from the location of the Current Semantic Value 1008 on the tag's underlying domain.

(4) Current Semantic Value 1008 may be calculated from other values or may be directly requested from the client 106. When a Current Numeric Value 1006 is recorded instead of a Current Semantic Value 1008, the Current Semantic Value 1008 may be determined by the relative magnitude of the Current Numeric Value 1006 within the context of the tag's underlying domain.

(5) Current Semantic Truth Value 1010—When a Current Semantic Truth Value 1010 is calculated, the degree to which the numeric value is represented by the Current Semantic Value 1008 may be represented on a scale from 0.0 to 1.0, with 0.0 indicating no representation to 1.0 indicating complete representation. The Current Semantic Truth Value 1010 may represent either the degree to which the Current Numeric Value 1006 is represented by the Current Semantic Value 1008 or the truthfulness of the assertion of the Current Semantic Value 1008.

Data Structures for Profiles and Data Tagging

Figure 11:
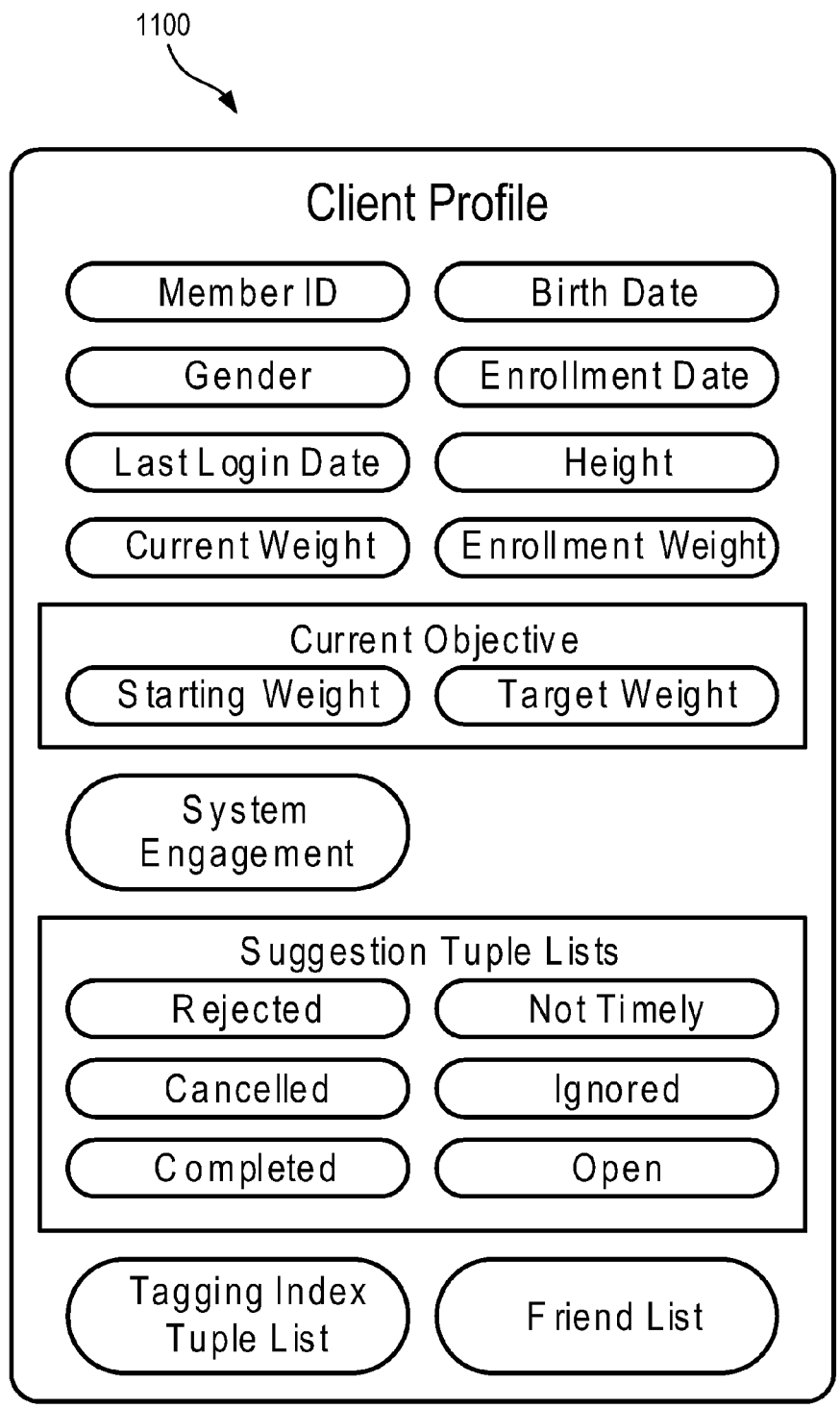
FIG. 11 illustrates a Client Profile data structure for storing client-specific information according to an example described herein.

FIG. 11 illustrates a Client Profile 1100 data structure for storing client-specific information, according to an example described herein. A Client Profile 1100 may contain the following components: (1) a Client ID, (2) a Gender, (3) a Birth Date, (4) a Date of Enrollment, (5) a Date of Last Login, (6) a Height, (8) an Enrollment Weight, (9) a Current Objective Starting Weight, (10) a Current Objective Target Weight, (11) a Level of System Engagement, (12) a list of rejected Prior Suggestion Tuples, (13) a list of ignored Prior Suggestion Tuples, (14) a list of cancelled Prior Suggestion Tuples, (15) a list of open Prior Suggestion Tuples, (16) a list of completed Prior Suggestion Tuples, (17) a list of Tagging Index Tuples, and (18) a list of Supporters.

(1) Client ID may be a machine-generated unique identity (usually a static, non-repeating, positive integer) of the actual client record located in the database.

(2) Gender may be the gender of the client 106, as recorded in the database.

(3) Birth Date may be the birth date of the client 106, as recorded in the database. Birth Date may be used to determine dynamically the client's age at any point in time.

(4) Date of Enrollment may be the date on which the client 106 first enrolled in the system, and may be used to determine such metrics as "relative experience," "level of system activity," etc.

(5) Date of Last Login may be the date and time on which the client 106 last logged into the system, and may be used to determine such metrics as "level of system activity," "time since last suggestions were delivered," etc.

(6) Height may be the height of the client 106, as recorded in the database.

(7) Current Weight may be the current weight of the client 106 as reported by the client 106 during the current or most recent session, during which weight was updated.

(8) Enrollment Weight may be the weight of the client 106 at the time of enrollment into the system, as recorded in the database.

(9) Current Objective Starting Weight may be the starting weight of the client 106 when a new Current Objective and its accompanying goals and objectives are set.

(10) Current Objective Target Weight may be the target weight of the client 106 under the current goals and objectives.

(11) System Engagement may be a metric of the current level of engagement of the client 106 with the system. This metric may be calculated from frequency of logins, last login, acceptance and completion of suggestions, progress toward goals and objectives, etc.

(12) The list of rejected Prior Suggestion Tuples 900—Each Prior Suggestion Tuple 900 in the list may represent a suggestion that was rejected by the client 106. The list may be ordered by recency of suggestion.

(13) The list of ignored Prior Suggestion Tuples 900—Each Prior Suggestion Tuple 900 in the list may represent a suggestion that was ignored by the client 106. The list may be ordered by recency of suggestion.

(14) The list of cancelled Prior Suggestion Tuples 900—Each Prior Suggestion Tuple 900 in the list may represent a suggestion that was cancelled by the client 106. The list may be ordered by recency of suggestion.

(15) The list of open Prior Suggestion Tuples 900—Each Prior Suggestion Tuple 900 in the list may represent a suggestion that was accepted by the client 106, but has not yet been closed (i.e., completed or cancelled) by the client 106. The list may be ordered by recency of suggestion.

(16) The list of completed Prior Suggestion Tuples 900—Each Prior Suggestion Tuple 900 in the list may represent a suggestion that was accepted by the client 106 and has been completed by the client 106.

(17) The list of Tagging Index Tuples 1000—For each general and content-type specific tag, there may be a corresponding Tagging Index Tuple 1000 in each Client Profile 1100; the Tagging Index Tuple 1000 may capture the current index of the client 106 as it applies to its tagging counterpart. This list may contain those Tagging Index Tuples 1000, and may be used to calculate the Compatibility Threshold 856 component of the Semantic Tagging Tuple 850 (as referenced in FIG. 8B). Additionally, a number of Tagging Index Tuples 1000 may be defined that may aid the content suggestion engine 102 in determining whether a particular suggestion may be appropriate at any given time. These indices are generally calculated in real-time based upon the historical data of the client 106.

Examples of possible Tagging Index Tuples 1000 may include a Difficulty Index, an Economic Index, a Restriction Index, a Success Index, a Duration Index, and a Social Index.

Figure 12:
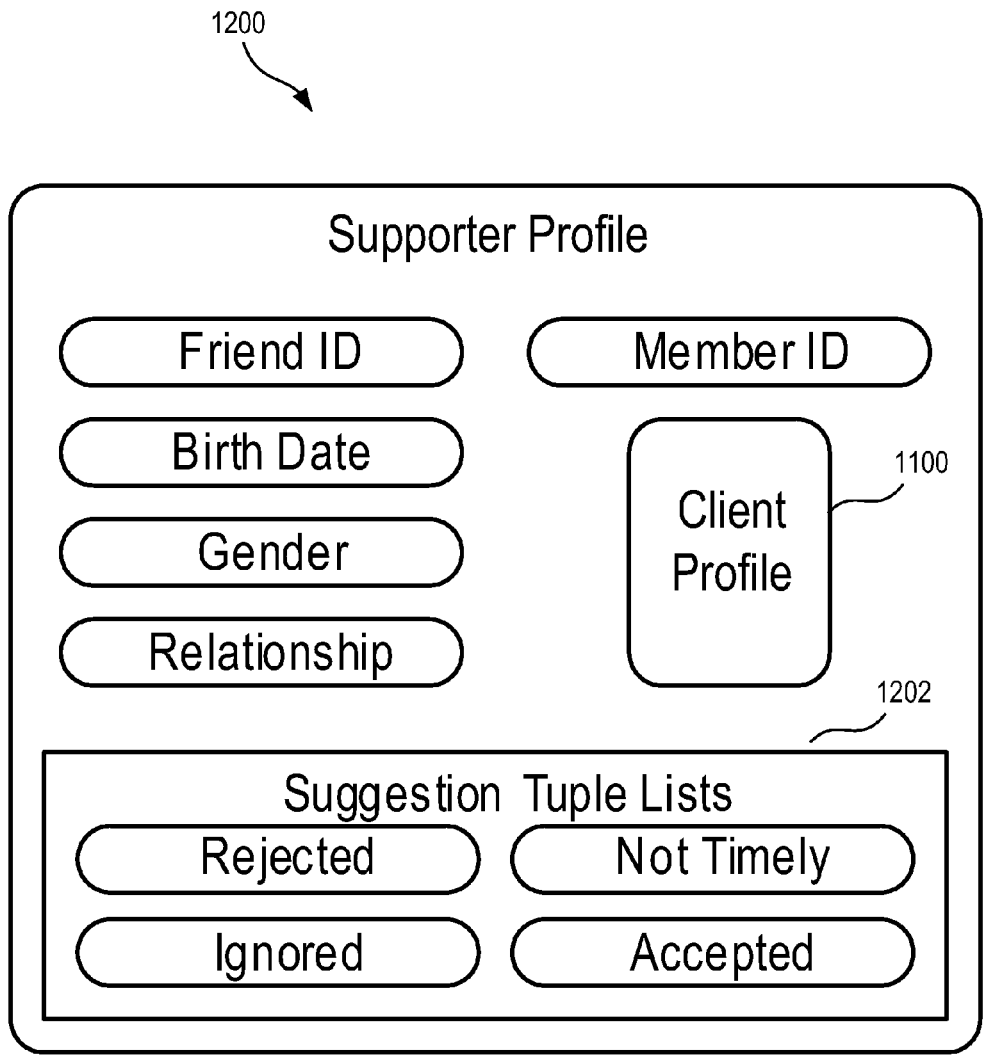
FIG. 12 illustrates a Supporter Profile data structure for storing supporter-specific information according to an example described herein.

(18) The list of Supporters may contain references to instances of the Supporter Profile (as referenced in FIG. 12).

FIG. 12 illustrates a Supporter Profile 1200 data structure for storing supporter-specific information, according to an example described herein. The Supporter Profile 1200 data structure may serve a function similar to that of the Client Profile 1100 data structure. Although similar to the Client Profile 1100 data structure, the Supporter Profile 1200 data structure may be simpler and may be used to generate suggestions for supporters to offer to clients.

The Supporter Profile 1200 data structure may include the following components: (1) a Supporter ID, (2) a Client ID, (3) a Birth Date, (4) a Gender, (5) a Relationship to Client, (6) a Client Profile 1100, (7) a list of rejected Prior Suggestion Tuples, (8) a list of ignored Prior Suggestion Tuples, and (9) a list of accepted Prior Suggestion Tuples.

(1) Supporter ID may be a machine-generated unique identity (usually a static, non-repeating, positive integer) of the actual supporter record located in the database.

(2) Client ID may be the Client ID of the client 106, to which one or more supporters are assigned. A Client ID may be a machine-generated unique identity (usually a static, non-repeating, positive integer) of the actual client record located in the database.

(3) Birth Date may be the supporter's birth date, as recorded in the database. Birth Date may be used to determine dynamically the supporter's age at any point in time.

(4) Gender may be the supporter's gender, as recorded in the database.

(5) Relationship to Client may represent the supporter's relationship to the client 106.

(6) Client Profile 1100 may be a reference to the Client Profile 1100 data structure (as referenced in FIG. 11) for the supporter's client.

(7) The list of rejected Prior Suggestion Tuples 900—Each Prior Suggestion Tuple 900 in the list may represent a suggestion that was rejected by the supporter (or the client 106). The list may be ordered by recency of suggestion.

(8) The list of ignored Prior Suggestion Tuples 900—Each Prior Suggestion Tuple 900 in the list may represent a suggestion that was ignored by the supporter (or the client 106). The list may be ordered by recency of suggestion.

(9) The list of accepted Prior Suggestion Tuples 900—Each Prior Suggestion Tuple 900 in the list may represent a suggestion that was accepted by the supporter and delivered to the client 106.

In further examples, the information system may match a client human user to supporter human users in a social network defined by the supporters. The supporter human users may be used to route one or more action statements, selected by the content suggestion engine based on a tag value associated with the action statements. The client may be matched to the supporter users by matching tags that correspond to characteristics of the client with tags corresponding to characteristics of the respective supporter users. The supporters may filter, refine and place the action statement and associated content in a more meaningful context by providing direct interaction and delivery of the content to the client.

Figure 13:
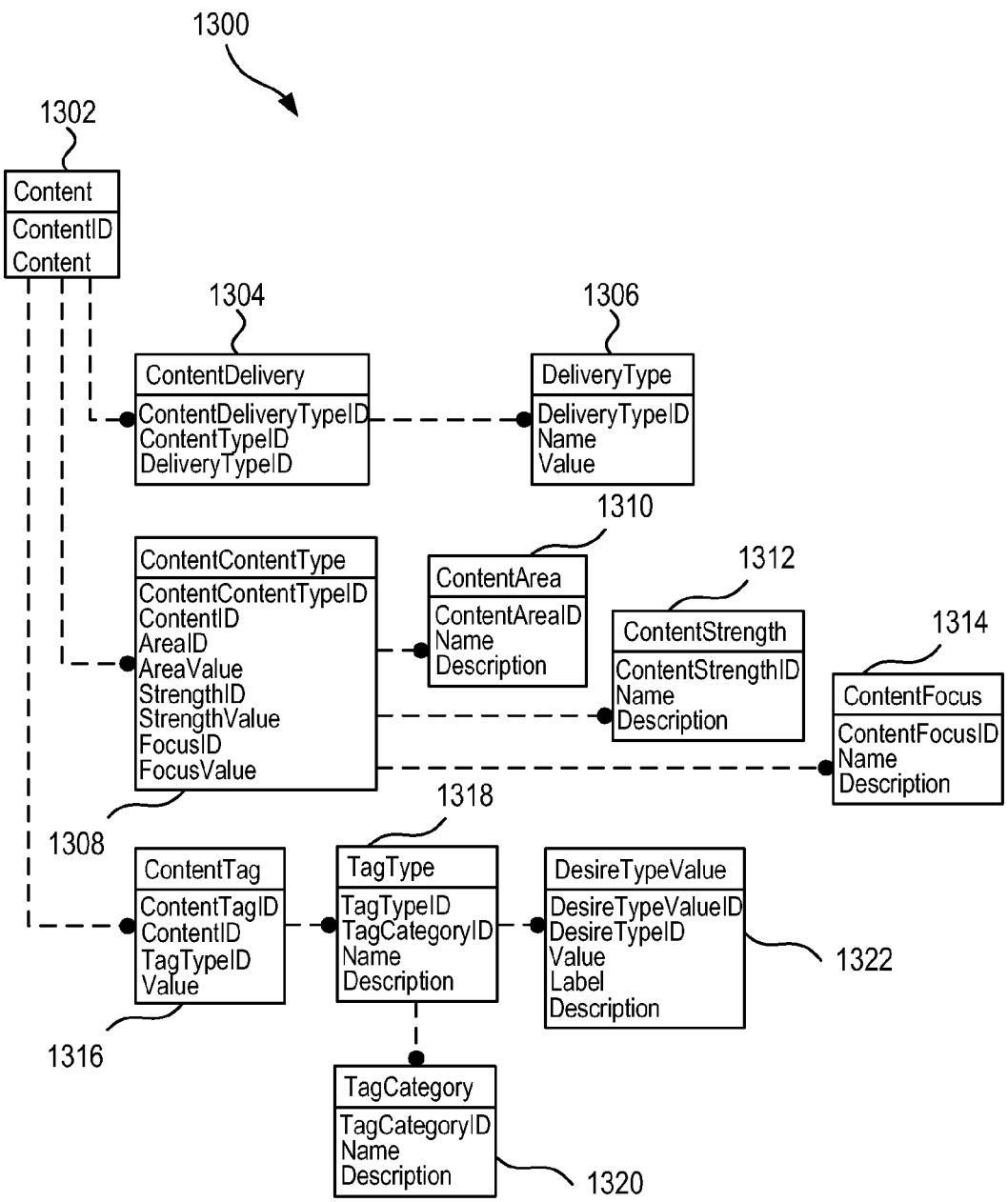
FIG. 13 illustrates an object-relational diagram for storing content and content tagging according to an example described herein.

FIG. 13 illustrates an object-relational diagram 1300 for storing a content item and associating the content item with tagging and content attributes, according to an example described herein. In the object-relational diagram 1300, each box may represent a table in a database. Static information pertaining to a piece of content may be stored in the database in a manner that allows for efficient storage and rapid search and retrieval.

The first box represents the Content table 1302. In object modeling terms, this is the main class in the object-relational diagram 1300.

The other boxes, ContentDelivery 1304, ContentContentType 1308, and ContentTag 1316 represent classes that may be contained by the Content class 1302. An instance of the Content class 1302 may contain instances of classes ContentDelivery 1304, ContentContentType 1308, and ContentTag 1316. The instances of these classes may be contained in lists (e.g., a listing 718 of Content Type Tuples may be implemented as a list of instances of the ContentContentType class 1308).

The other boxes DeliveryType 1306, ContentArea 1310, ContentStrength 1312, ContentFocus 1314, and TagType 1318 represent types of tags within predefined categories that may be assigned to a piece of content. These may be considered "lookup" tables, and may generally be implemented as utility classes in the object model.

The other boxes TagCategory 1320 and DesireTypeValue 1322 represent fixed labels and values from which the value stored in the corresponding green boxes may be selected, or the tags are filtered. These may be "lookup" tables and may generally be implemented as utility classes in the object model.

Application of Data Tagging to Suggested Actions

FIG. 14 illustrates a user interface 1400 of a tagging facility for adding tagging content items according to an example described herein. The user interface 1400 of the tagging facility may list the content items and tag categories used in the system. The tagging facility may be used by an administrative user or other skilled person to input and define new tags in the various input fields.

FIG. 15 illustrates a second user interface 1500 of a tagging facility. The tagging facility may enable a user to search for content, and may allow a user to add, edit, or delete content. In some embodiments, a particular piece of content may not be deleted after the content has been used. In some embodiments, a particular piece of content can be disabled or hidden from the content suggestion engine 102.

The user interfaces 1400, 1500 of the may allow a tagger to edit content and content properties, to assign types, and to tag specific action statements and other content items. The grouping of types and tags into categories may ease the tagging process and may facilitate quick, accurate, and consistent tagging of content. Content, along with its constituent properties, may be complex, therefore necessitating a graphical user interface for form-based editing to facilitate tagging of multidimensional content. The tagging facility enables selecting and assigning particular behavior/psychological related tags to a particular action statement.

As one example, the tagging may enable: creation of suggestions to include an action statement with an additional description; addition of pre- and post-"personalization" statements; application of the suggestions by trained "Taggers"; and performance of a quality inspection review by trained persons. As a result of the tagging in the user interfaces 1400, 1500, suggestions can be loaded into a database available to clients and supporters.

Example Technique and System Implementations

Figure 16:
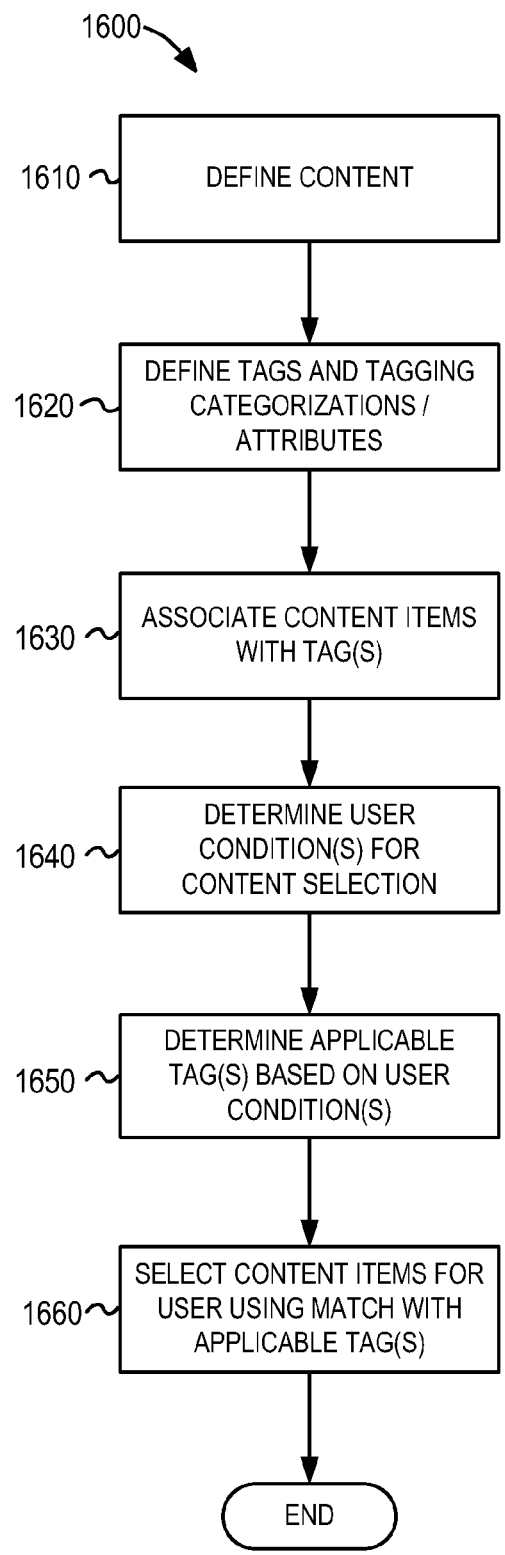
FIG. 16 illustrates an example flowchart of a method for applying tagging to suggested action content according to an example described herein.

FIG. 16 illustrates a flowchart of a method 1600 for tagging data for consumption by a content suggestion engine or other component of an information system. As depicted, the operations include the definition of content (operation 1610) within the information system. The content, for example, may include various action statements, pre- and post-statements, combinations of action statements and pre/post statements, in textual or multimedia form.

Additionally, the operations include the definition of tags and relevant tagging categorizations and attributes (operation 1620) within the information system. This may include the establishment of a hierarchical or relational tagging structure, to classify associated attributes or characteristics within the tags.

Next, further operations include the association of the respective content items with one or more tags (operation 1630). This may include the assignment of various tags based on the content item itself, provided from human or automated classifications.

Upon establishment of the content items and tags, and tagging operations upon the content items, the content items may be retrieved by tag. Appropriate retrieval operations may include the retrieval of appropriate content based on one or more tags that match the current condition of the user. For example, specific operations may include determining the one or more user conditions for content selection (operation 1640), determining applicable tags based on the one or more user conditions (operation 1650), and selecting one or more content items for the user, from the information system, using content matching the applicable tags (operation 1660). The user conditions for content selection in particular may be related to the achievement or progress for the overall or environmental goal. Thus, if a particular user encounters some user condition (e.g., obstacle or hindrance) to achieve the goal, applicable tags to address the user condition may be selected, and accordingly content items matching the applicable tag (addressing the user condition) may be retrieved.

Figure 17:
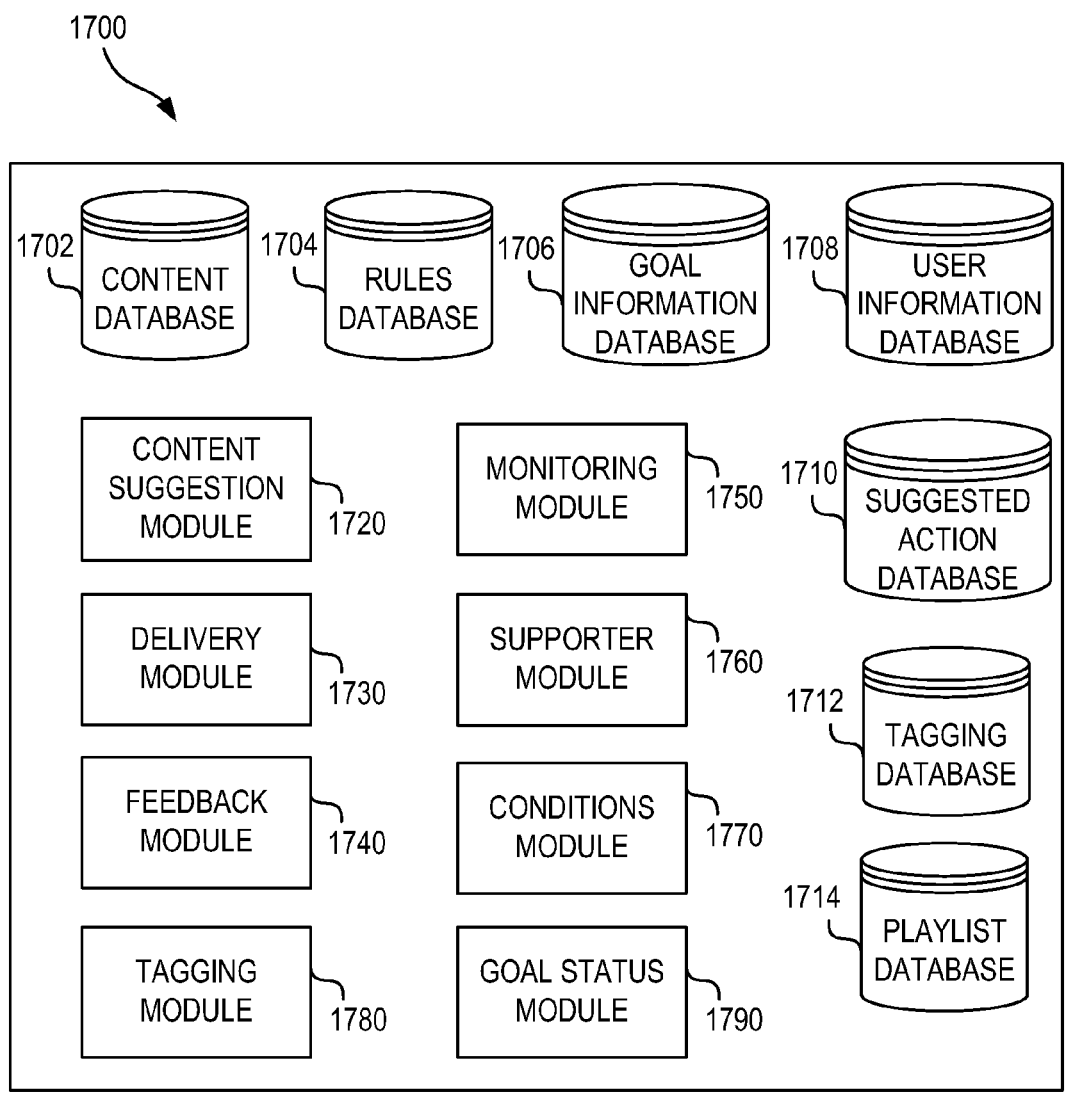
FIG. 17 illustrates an example system configuration of an information system arranged to provide suggested content according to an example described herein.
Figure 18:
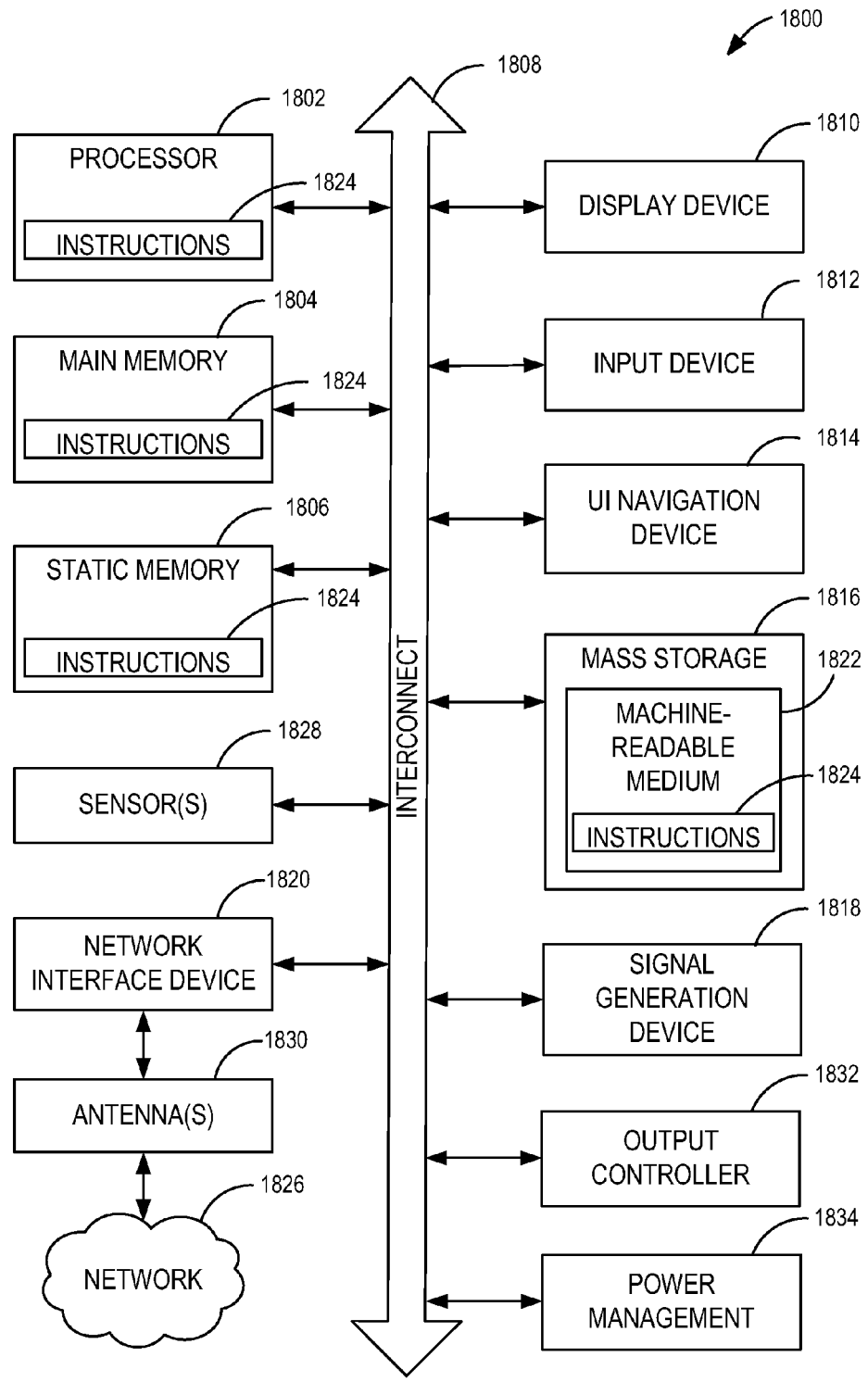
FIG. 18 illustrates an example of a computer system to implement techniques and system configurations according to an example described herein.

FIG. 17 illustrates an example of a system configuration of an information system 1700 configured to provide content. The information system 1700 can include a content database 1702, a rules database 1704, a goal information database 1706, a client information database 1708, a suggested action database 1710, a tagging database 1712, and a playlist database 1714.

The content database 1702 can include information from external sources, such as the supporter network 104, a professional expert working in a field relevant to a goal 204, other databases, or a combination thereof, among others. The rules database 1704 can include rules for formatting and providing personalized suggested actions to the client 106. Such rules can include timing restrictions, wording suggestions or restrictions, or suggested action restrictions (e.g., a suggested action message 402 with a certain tag should not be presented to a specific client).

The goal information database 1706 can include data relevant to getting the client 106 to achieve a particular goal 204. The goal information can include certain activities that are essential to achieving a goal 204 (e.g., running a marathon requires the client to run to achieve the goal 204), recommended for achieving the goal 204 (e.g., stretching muscles and breathing exercises are helpful, but not essential, in training for a marathon), fun (e.g., things to keep the client 106 in a positive state of mind or reward the client 106 for their hard work or achievements), or a combination thereof, among others.

The client information database 1708 can include information gained from questionnaires or learned through the client 106 or supporters in the supporter network 104 using the system. The client information database 1708 can include information about all users of the system including supporters, clients 106, administrators of the system, or potential clients, among others. The suggested action database 1710 can include suggested actions such as suggested action message 402 including pre-statements 404, action statements 406, and post-statements 408. The suggested action database 1710 can also include a record of which client has completed which suggested action message 402, when the client 106 completed the suggested action message 402, or how long it has been since the system recommend that suggested action message 402 to the client 106.

The tagging database 1712 can include a record of all the tags and tagging relationships that have been created for suggested actions, playlists, or programs, and which suggested actions, programs, or playlists the tag is associated with. The playlist database 1714 may be used to generate a playlist of tagged content (such as suggested actions), provided in accordance with operations of the content suggestion module 1720.

While FIG. 17 shows seven separate databases 1702-1712, the information contained within the databases may be contained within any number of databases. For example, the information in the tagging, suggested action, and playlist databases 1710, 1712, 1714 might be combined into a single database.

The information system 1700 can include one or more modules including a content suggestion module 1720, a delivery module 1730, a feedback module 1740, a monitoring module 1750, a supporter module 1760, a conditions module 1770, a tagging module 1780, or a goal status module 1790. The content suggestion module 1720 can receive suggested actions or have access to the suggested action database 1710. The content suggestion module 1720 can include the filter(s) 410 and the weight(s) 412, such as to allow the content suggestion module 1720 to filter, prioritize, or present suggested actions to the client 106.

The delivery module 1730 can present at least one suggested action message 402 or associated message to the supporter network 104 or the client 106, such as at a certain relevant time. The delivery module 1730 can be configured to modify or amend the suggested action message 402 or message that is delivered so as to be appropriate for the client 106. Such a configuration can make the client 106 more likely to complete the suggested action message 402.

The feedback module 1740 can be configured to receive feedback about suggested actions from a client 106, process the feedback, and send the processed feedback to the client information database 1708, rules database 1704, or content database 1702, or suggested action database 1710.

The monitoring module 1750 can be configured to monitor a client's progress towards their goal(s) 204, a client's progress on completing a suggested action message 402, program, or playlist, and can provide the delivery module 1730 with information relevant to what messages (e.g., prompts, reminders, or encouragements) should be sent to the client 106.

The supporter module 1760 can be configured to provide the supporter network 104 with the ability to make suggestions for a suggested action message 402 to present to the client 106, provide information relevant to getting the client 106 to their goal 204 (e.g., likes, dislikes, barriers 214, or incentives 216 for the client 106, etc.), suggest messages to send to the client 106 that can be modified by the delivery module 1730, or suggest tags that should be associated with the client 106.

The conditions module 1770 can be configured to maintain relevant information from the ecosystem of conditions 212 and the client data conditions 108 that are relevant to the selection and delivery of relevant content. This may include direct or derived contextual data, or data relevant to barriers and incentives. For example, the contextual information maintained in conditions module may provide input for rules to express the conditions to deliver content to the proper user, at the proper time, in the proper context, and with the proper communication medium.

The tagging module 1780 can be configured to maintain and manage tagging process to transform unstructured data (not necessarily relevant to a particular user) stored among the various databases into structured data (relevant to a particular user) for use in achieving a goal. The tagging module 1780 may be used to apply tags to various content stored in the content database 1702; to classify tags to rules stored in the rules database 1704; and to associate tags with data in the goal information database 1706, client information database 1708, and suggested action database 1710.

Further, the goal status module 1790 can be configured to maintain and manage a user's goal status and operations related to the achievement of the user's goal status. This may integrate in connection with the tagging module 1780 to provide particular tags to items based on a user's goal status and other information stored in the goal information database 1706.

Computing System Architectures and Example Implementations

FIG. 10 is a block diagram illustrating an example computer system machine upon which any one or more of the methodologies herein discussed may be run. Computer system 1800 may be embodied as a computing device, providing operations of the content suggestion engine 102 or information system 1700 (from FIGS. 1 and 17), or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a set-top box (STB), a gaming console, a Personal Digital Assistant (PDA), a mobile telephone or smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1800 includes a processor 1802 (e.g., a central processing unit (CPU), a graphics processing unit (GPU) or both), a main memory 1804 and a static memory 1806, which communicate with each other via an interconnect 1808 (e.g., a link, a bus, etc.). The computer system 1800 may further include a video display unit 1810, an alphanumeric input device 1812 (e.g., a keyboard), and a user interface (UI) navigation device 1814 (e.g., a mouse). In one embodiment, the video display unit 1810, input device 1812 and UI navigation device 1814 are a touch screen display. The computer system 1800 may additionally include a storage device 1816 (e.g., a drive unit), a signal generation device 1818 (e.g., a speaker), an output controller 1832, a power management controller 1834, and a network interface device 1820 (which may include or operably communicate with one or more antennas 1830, transceivers, or other wireless communications hardware), and one or more sensors 1828, such as a GPS sensor, compass, location sensor, accelerometer, or other sensor.

The storage device 1816 includes a machine-readable medium 1822 on which is stored one or more sets of data structures and instructions 1824 (e.g., software) embodying or utilized by any one or more of the methodologies or functions described herein. The instructions 1824 may also reside, completely or at least partially, within the main memory 1804, static memory 1806, and/or within the processor 1802 during execution thereof by the computer system 1800, with the main memory 1804, static memory 1806, and the processor 1802 also constituting machine-readable media.

While the machine-readable medium 1822 is illustrated in an example embodiment to be a single medium, the term "machine-readable medium" may include a single medium or multiple media (e.g., a centralized or distributed database, and/or associated caches and servers) that store the one or more instructions 1824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1824 may further be transmitted or received over a communications network 1826 using a transmission medium via the network interface device 1820 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the suggestion engine 102 can include or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Embodiments may also be implemented as instructions stored on a computer-readable storage device or storage medium, which may be read and executed by at least one processor to perform the operations described herein. A computer-readable storage device or storage medium may include any non-transitory mechanism for storing information in a form readable by a machine (e.g., a computer). For example, a computer-readable storage device or storage medium may include read-only memory (ROM), random-access memory (RAM), magnetic disk storage media, optical storage media, flash-memory devices, and other storage devices and media. In some embodiments, the electronic devices and computing systems described herein may include one or more processors and may be configured with instructions stored on a computer-readable storage device.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments include the following, non-limiting configurations. Each of the following non-limiting examples can stand on its own, or can be combined in any permutation or combination with any one or more of the other examples provided below or throughout the present disclosure.

A first example can include the subject matter (such as an apparatus, a method, a means for performing acts, or a machine readable medium including instructions that, when performed by the machine, that can cause the machine to perform acts), for facilitating communications from a goal-based information system, comprising: obtaining an action statement stored in a database of unstructured data; selecting a tag from a hierarchy of tags, wherein the tag relates to a characteristic of a human action described by the action statement; and associating the action statement with the tag in a database of structured data, for use by a content suggestion engine; wherein the tag provides information to the content suggestion engine to select and incorporate the action statement within a content suggestion generated for a human user, and wherein the human action described by the action statement is selected by the content suggestion engine to encourage progress towards a goal defined by the human user.

A second example can include, or can optionally be combined with the subject matter of one or any combination of the first example, to include subject matter (such as an apparatus, a method, a means for performing acts, or a machine readable medium including instructions that, when performed by the machine, that can cause the machine to perform acts), for an information system, comprising: a tagging module implemented using a processor, the tagging module configured to: associate multiple tags to respective content items; and a content suggestion module implemented using the processor, the content suggestion module configured to: determine a subset of the content items being related to a goal of a human user; and select a content item from the subset of content items for suggestion to the human user, based on a match of profile characteristics stored for the human user to the multiple tags associated with the subset of content items.

A third example can include, or can optionally be combined with the subject matter of one or any combination of the first example and the second example, to include subject matter (such as an apparatus, a method, a means for performing acts, or a machine readable medium including instructions that, when performed by the machine, that can cause the machine to perform acts), for instructions of an computing device, configured to cause the computing device to: generate a tagging interface for display within a graphical user interface accessible by an administrative user to: define a plurality of tags in a hierarchical categorization for application to respective content items; and apply the plurality of tags to the respective content items; select content items using a content suggestion engine, the content suggestion engine configured to: determine a condition of a client user indicated by a user profile associated with the client user; determine an applicable tag based on the conditions of the client user indicated by the user profile; and select a subset of the content items for delivery to a client user using the applicable tag; and generate a content interface for display within a graphical user interface accessible by the client user to: display the subset of the content items to the client user using the graphical user interface.

The following claims are hereby incorporated into the detailed description, with each claim and identified combination of claims standing on its own as a separate example.

What is claimed is:

1. A method of tagging data for use by a content suggestion engine, the method comprising:
    defining a plurality of tags in a hierarchical categorization, the plurality of tags defined for application to respective content items of a plurality of content items;
    obtaining an action statement stored in a database of unstructured data;
    processing a selection of a particular tag from the plurality of tags to apply to the action statement, wherein the particular tag relates to a characteristic of a human action described by the action statement; and
    associating the action statement with the particular tag in a database of structured data, for use by a content suggestion engine;
    wherein the particular tag provides information to the content suggestion engine to select the action statement from the plurality of content items using the content suggestion engine, with operations performed by the content suggestion engine that:
    determine a condition of a human user indicated by a user profile associated with the human user;
    determine an applicable tag based on the condition of the human user indicated by the user profile, the applicable tag matching the particular tag; and
    select a subset of the plurality of content items using the applicable tag, the subset including the action statement; and
    incorporate the action statement within a content suggestion generated for the human user;
    wherein the human action described by the action statement is selected by the content suggestion engine to encourage progress towards a goal defined by the human user; and
    wherein the content suggestion is output to a display of a computing device with use of a graphical user interface.

2. The method of claim 1, further comprising:
    selecting the action statement using the content suggestion engine, the action statement being selected by the content suggestion engine based on a match of the particular tag to a characteristic of the human user, wherein the hierarchy of tags defines groupings of tags correlating to categories of human behaviors and actions.

3. The method of claim 2, wherein the characteristic of the human user is determined from a profile of the human user, and wherein the action statement is selected by the content suggestion engine based on a match of the characteristic of the human action to the profile of the human user.

4. The method of claim 3, wherein the action statement is selected by the content suggestion engine from a plurality of action statements matching the particular tag.

5. The method of claim 2, wherein selecting the action statement includes the content suggestion engine filtering action statements by multiple filter tags, the filter tags corresponding to actions previously completed by the human user, actions previously rejected by the human user, or restrictions of the human user.

6. The method of claim 5, wherein selecting the action statement includes the content suggestion engine providing a selection preference to action statements using a weighting tag, the weighting tag corresponding to a preference of the human user.

7. The method of claim 2, further comprising:
    selecting a pre-statement for the action statement using the particular tag;
    selecting a post-statement for the action statement using the particular tag; and
    generating a content item for delivery to the display of the computing device using the pre-statement, the action statement, and the post-statement.

8. The method of claim 1, wherein the particular tag defines multiple behavior change attributes relevant to behavior of the human user.

9. The method of claim 1, wherein the particular tag corresponds to a characteristic of the human user stored in a user profile maintained for the human user.

10. The method of claim 1, further comprising:
    selecting the action statement based on the particular tag using the content suggestion engine; and
    matching the human user to supporter human users in a social network;
    wherein the supporter human users are used to route and modify the action statement to be output to the display of the computing device.

11. The method of claim 10, wherein the human user is matched to the supporter users based on matching tags corresponding to characteristics of the human user with tags corresponding to characteristics of the supporter users.

12. An information system, comprising:
    a tagging module implemented using a processor, the tagging module configured to:
        define a plurality of tags in a hierarchical categorization, the plurality of tags being defined for application to respective content items, wherein at least one tag of the plurality of tags relates to a characteristic of a human;
        associate the at least one tag of the plurality of tags to the respective content items; and
    a content suggestion module implemented using the processor, the content suggestion module configured to:
        determine a condition of a human user indicated by a user profile associated with the human user;
        determine an applicable tag of the plurality of tags based on the condition of the human user indicated by the user profile;
        select two or more of the respective content items using the applicable tag, the two or more of the respective content items related to a goal of the human user; and
        select a content item from the two or more of the respective content items for output on a display of a computing device, based on a match of profile characteristics stored for the human user to the at least one tag of the plurality of tags associated with the two or more of the respective content items.

13. The information system of claim 12, further comprising:
    a goal status module implemented using the processor, the goal status module configured to determine information for the goal of the human user.

14. The information system of claim 13, further comprising:
    a monitoring module implemented using the processor, the monitoring module configured to monitor activity by the human user to determine a completion status of the goal of the human user.

15. The information system of claim 12, further comprising:
- a delivery module implemented using the processor, the delivery module configured to provide the content item selected from the two or more of the respective content items to the human user using the display of the computing device;
- a feedback module implemented using the processor, the feedback module configured to collect feedback from the human user on the content item selected from the two or more of the respective content items.

16. The information system of claim 15, further comprising:
- a content database configured to store the respective content items;
- a goal information database configured to store data on an accomplishment status of the goal by the human user;
- a user information database configured to store the profile characteristics for the human user;
- a tagging database configured to store the plurality of tags; and
- a suggestion action database configured to store suggested actions of the respective content items.

17. The information system of claim 16, further comprising:
- a playlist database configured to store a playlist of tagged content;
- wherein the delivery module is further configured to provide content items from the playlist of tagged content.

18. A non-transitory machine-readable storage medium comprising a plurality of instructions, which when executed on a computing device, cause the computing device to:
- generate a tagging interface for display within a graphical user interface accessible by an administrative user to:
  - define a plurality of tags in a hierarchical categorization, the plurality of tags defined for application to respective content items; and
  - apply the plurality of tags to the respective content items;
- select two or more content items of the respective content items using a content suggestion engine, the content suggestion engine configured to:
  - determine a condition of a client user indicated by a user profile associated with the client user;
  - determine an applicable tag based on the condition of the client user indicated by the user profile; and
  - select a subset of the two or more content items for presentation to a client user using the applicable tag; and
- generate a content interface for display within a graphical user interface accessible by the client user to:
  - display the subset of the two or more content items to the client user using the graphical user interface.

19. The machine-readable storage medium of claim 18, wherein operations of the content suggestion engine to determine the condition of a client user include matching multiple characteristics of the user profile to characteristics associated with respective groupings of tags in the hierarchical categorization;
- wherein operations of the content suggestion engine to determine the applicable tag based on the condition of the client user include selecting the applicable tag from the respective groupings of tags; and
- wherein operations of the content suggestion engine to select the subset of the two or more content items for presentation to the client user include adding a weight to tags associated with content items rated favorably by the client user, and filter content items having tags correlating to a restriction by the client user.

20. The machine-readable storage medium of claim 18, wherein operations to define the plurality of tags in the hierarchical categorization include establishing an assignment of the tags to multiple tag values; and
- wherein operations of the content suggestion engine to select the subset of the two or more content items for presentation to the client user include determining current contextual values for the client user and selecting tags based on the current contextual values.

21. The machine-readable storage medium of claim 18, wherein instructions to select two or more content items of the respective content items using the content suggestion engine include instructions, which when executed by the computing device, cause the computing device to select a pre-statement for each of the two or more content items and select a post-statement for each of the two or more content items based on the applicable tag.

22. The machine-readable storage medium of claim 18, wherein instructions to generate the content interface for display within the graphical user interface accessible by the client user include instructions, which when executed by the computing device, cause the computing device to receive responses to the subset of the two or more content items to further restrict selection of the two or more content items.

23. The machine-readable storage medium of claim 18, wherein instructions to generate the content interface for display within the graphical user interface accessible by the client user include instructions, which when executed by the computing device, cause the computing device to display information related to a defined goal of the client user based on the applicable tag.

* * * * *

UNITED STATES PATENT AND TRADEMARK OFFICE
CERTIFICATE OF CORRECTION

| | | |
|---|---|---|
| PATENT NO. | : 9,183,262 B2 | Page 1 of 1 |
| APPLICATION NO. | : 13/801315 | |
| DATED | : November 10, 2015 | |
| INVENTOR(S) | : Brust et al. | |

It is certified that error appears in the above-identified patent and that said Letters Patent is hereby corrected as shown below:

In the claims,

In column 39, line 7, in Claim 15, after "device;", insert --and--, therefor

Signed and Sealed this
Sixteenth Day of February, 2016

Michelle K. Lee
*Director of the United States Patent and Trademark Office*